United States Patent
Nair et al.

(10) Patent No.: US 9,650,360 B2
(45) Date of Patent: May 16, 2017

(54) ANTI-MYCOBACTERIAL DRUGS AGAINST TUBERCULOSIS

(71) Applicant: UNIVERSITY OF GEORGIA RESEARCH FOUNDATION, INC., Athens, GA (US)

(72) Inventors: Vasu Nair, Athens, GA (US); Maurice O. Okello, Athens, GA (US); Machhindra G. Gund, Athens, GA (US); Byung I. Seo, Hoschton, GA (US); Pankajkumar R. Singh, Maharastra (IN); Naveen K. Mangu, Athens, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 34 days.

(21) Appl. No.: 14/388,404

(22) PCT Filed: Mar. 13, 2013

(86) PCT No.: PCT/US2013/030687
§ 371 (c)(1),
(2) Date: Sep. 26, 2014

(87) PCT Pub. No.: WO2013/148174
PCT Pub. Date: Oct. 3, 2013

(65) Prior Publication Data
US 2015/0050237 A1  Feb. 19, 2015

Related U.S. Application Data

(60) Provisional application No. 61/618,707, filed on Mar. 31, 2012.

(51) Int. Cl.
| | | |
|---|---|---|
| *A01N 43/40* | (2006.01) | |
| *A61K 31/435* | (2006.01) | |
| *C07D 401/12* | (2006.01) | |
| *C07D 213/64* | (2006.01) | |
| *A61K 31/496* | (2006.01) | |
| *A61K 45/06* | (2006.01) | |

(52) U.S. Cl.
CPC .......... *C07D 401/12* (2013.01); *A61K 31/496* (2013.01); *A61K 45/06* (2013.01); *C07D 213/64* (2013.01)

(58) Field of Classification Search
None
See application file for complete search history.

(56) References Cited

U.S. PATENT DOCUMENTS

| | | |
|---|---|---|
| 7,250,421 B2 | 7/2007 | Nair et al. |
| 7,569,573 B2 | 8/2009 | Nair et al. |
| 7,888,375 B2 | 2/2011 | Nair et al. |
| 8,703,801 B2 | 4/2014 | Nair et al. |

FOREIGN PATENT DOCUMENTS

| | | |
|---|---|---|
| WO | 0196308 A1 | 12/2001 |
| WO | 2011071849 A2 | 6/2011 |

OTHER PUBLICATIONS

Ernst, "The immunological life cycle of tuberculosis", Nat. Rev. Immun., 2012, vol. 12, pp. 581-591.*
Manjunatha et al., "Direct inhibitors of InhA are active against *Mycobacterium tuberculosis*", Sci.Transl.Med., 2015, vol. 7, No. 269, 269ra3.*
Byung I. Seo et al.,Discovely of Potent HIV Integrase Inhibitor that Leads to a Prodrug with Significant anti-HIV Activity. ACS Medicinal Chemistry Letters 2011, vol. 2 , No. 12, pp. 877-881.

* cited by examiner

*Primary Examiner* — Jeffrey S Lundgren
*Assistant Examiner* — Stephanie Springer
(74) *Attorney, Agent, or Firm* — Henry D. Coleman; R. Neil Sudol

(57) ABSTRACT

The present invention relates to the field of anti-mycobacterial therapeutics, in particular the treatment of tuberculosis, especially including pulmonary multidrug-resistant tuberculosis (MDR-TB), with applications in extensively drug-resistant tuberculosis (XDR-TB) and extremely drug-resistant tuberculosis (XXDR-TB), preferably in combination therapy.

33 Claims, No Drawings

_US 9,650,360 B2_

ANTI-MYCOBACTERIAL DRUGS AGAINST TUBERCULOSIS

RELATED APPLICATIONS AND GRANT SUPPORT

This application is a United States national phase application claiming the benefit of priority from international application no. PCT/US2013/030687, of identical title, filed on Mar. 13, 2013 which claims the benefit of priority from provisional application Ser. No. 61/618,707, filed Mar. 31, 2012, of identical title, the entire contents of each of said applications being incorporated by reference in its entirety herein.

The present invention was supported in the early phases of discovery through support from the National Institutes of Health under grant R01 AI 43181. Consequently, the government has certain rights in the invention.

FIELD OF THE INVENTION

The present invention relates to the field of anti-mycobacterial therapeutics, in particular the treatment of pulmonary multidrug-resistant tuberculosis (MDR-TB), with applications in extensively drug-resistant tuberculosis (XDR-TB) and extremely drug-resistant tuberculosis (XXDR-TB), preferably in combination therapy.

BACKGROUND AND DISCUSSION OF THE INVENTION

*Mycobacterium tuberculosis* (TB) is a contagious, largely pulmonary, disease that is spread through the air. Only a small number of TB bacilli are needed to cause an infection. Almost a third of the world's population is currently infected with TB. Of the people who are infected with TB but who are not infected with HIV, some 5-10% become sick or are infectious at some period during their lifetime (WHO Fact Sheet, November, 2010, WHO report 2011: Global Tuberculosis Control). People with HIV are much more likely to develop TB. An estimated 1.7 million people died from TB in 2009. Also, multidrug-resistant *M. tuberculosis*, MDR-TB, is spreading [Orenstein, et al., *Lancet Infect. Dis.* 9, 153-161 (2009); Russell, et al., *Science* 328, 852-856 (2010); Dye, et al., *Science* 328, 856-861; (2010)]. Further complicating the TB picture worldwide is the emergence of extensively drug-resistant tuberculosis, XDR-TB and extremely drug-resistant tuberculosis, XXDR-TB (WHO: Drug Resistant TB, 2012).

However, there have been relatively few new agents discovered in the last 40 years to treat TB [Aristoff, et al., *Tuberculosis* 90, 94-118 (2010), Koul., et al., *Nature* 469, 483-490 (2100)]. Among the most used TB drugs are rifampin and its analogs, isoniazid, pyrazinamide, ethambutol and fluoroquinolone. The drug pipeline today is relatively thin with only 10 new or repurposed drugs in clinical trials [Zumla, et al., *Nat. Rev. Drug Discov.* 11, 171-172 (2012); *New TB Drugs Website,* 2011, online; Sundaramurthi, et al., *Tuberculosis* 92, 133-138 (2012); Luetkemeyer, et al., *Am. J. Respir. Crit. Care Med.* 184, 1107-1113 (2011); Lienhardt, et al., *Curr. Opin. Pulm. Med.* 16, 186-193 (2010); Ma, et al., *Lancet,* 375, 2100-2109 (2010)]. One of those drugs [bedaquiline, also referred to as R207910, TMC207, Andries, et al., *Science* 307, 223-227 (2005), Koul, et al., CA2529265A1; Porstmann, F. R., et al., WO2006125769A1; Brickner, S. J., et al., WO2010026526A1; Devito, et al., WO2011139832A2] was approved by the FDA in December 2012 as part of a combination treatment regimen for MDR-TB (NDA 204-384). Examples of other drugs in the clinical phase of development include: gatifloxacin [Ma, et al., *Lancet* 375, 2100-2109 (2010), He, et al., CN102198138A, Patel, et al., WO2011101710A1, Ismail, et al., WO2012057599A1]; moxifloxacin [Ji, et al., *Antimicrob. Agents Chemother.* 42, 2066-2069 (1998), Miyazaki, et al., *Antimicrob. Agents Chemother.* 43, 85-89 (1999), Alvirez-Freites, et al., *Antimicrob. Agents Chemother.* 46, 1022-1025 (2002), Bosche, et al., WO2000027398A1; McCarthy, et al., WO2003099229A2; Zeldis, et al., WO2010093588A1]; sudoterb [Ginsberg, Drugs 70, 2201-2214 (2010), Arora, et al., WO2004026828A1, Arora, et al., WO2006109323A1]; PNU100480 [Williams, et al., *Antimicrob. Agents Chemother.* 53, 1314-1319 (2009), Barbachyn, et al., WO9507271A1, Watts, et al., WO2002002121A2; Brickner, et al., WO2010026526A1, Wallis, WO2010122456A1]; AZD5847 [Williams, et al., *Antimicrob. Agents Chemother.* 53, 1314-1319 (2009), Kim, et al., WO2012144790A1]; SQ109 [Protopopova, et al., *J. Antimicrob. Chemother.* 56, 968-974 (2005), Sutcliffe, WO2007133803A2, Meng, Q., et al., CN101468958A]; OPC67683 [Singh, et al., *Science* 322, 1392-1395 (2008), Singh, et al., WO2007133803A2]; PA824 [Singh, et al., *Science* 322, 1392-1395 (2008), Sutcliffe, WO2007133803A2, Papadopoulou, et al., US20080076797A1, Singh, et al., WO2008005651A2, Devito, et al., WO2011139832A2].

MDR-TB is resistant to isoniazid and rifampin, the two drugs that are used commonly for drug-susceptible TB and with treatment-adherent TB patients. MDR-TB that has also developed resistance to one of the injectable second line TB drugs (kanamycin, capreomycin or amikacin) and also to a fluoroquinolone drug is classed as XDR-TB. XDR-TB can be treated with other second-line TB drugs, but the treatment is more difficult, more expensive and there may be more side effects. XXDR-TB is resistant to both first line and second line TB drugs and is extremely difficult to treat. In general, treatment for all drug-resistant TB can be complicated, lengthy and may be problematic, in part because of issues of toxicity.

Our research work on retroviral integrase inhibitors has led to the discovery of highly active compounds against a diverse set of primary HIV-1 isolates [Nair, et al., US 2012 0282218 A1, Nair, et al., PCT International Patent Application No. WO 2011/071849 A2, Nair, et al., ASM ICAAC Conference H2-801 (2011)]. In investigating the molecular modeling details of the mechanism of action of our active integrase inhibitors, it was apparent that these inhibitors had one common feature, i.e., they were all interacting with the DDE catalytic triad and also with two divalent magnesium ions in the catalytic core domain of HIV integrase. The DDE motif is essential for integrase catalysis [Nair, et al., *Rev. Med. Virol.* 17, 277-295 (2007), Nair, et al., *J. Med. Chem.* 49, 445-447 (2006), Frankel, et al., *Annu. Rev. Biochem.* 67, 1-25 (1998)]. However, our best integrase inhibitors of this class, while exhibiting potent anti-HIV activity [Nair, et al., US 2012 0282218 A1, Nair, et al., PCT International Patent Application No. WO 2011/071849 A2, Nair, et al., ASM ICAAC Conference H2-801 (2011], did not show as compelling a level of anti-MDR TB activity as the novel compounds of the current invention.

The catalytic core domain of DNA-dependent RNA polymerase (RNAP) of bacteria is conserved among cellular organisms [Archambault, et al., *Microbiol. Mol. Biol Rev.* 57, 703-724 (1993)]. Examination of the crystal structure [Zhang, et al., *Cell* 98, 811-824 (1999)] of the RNAP of

*Thermus acquaticus* (a model for TB RNAP), with bound rifampin, a first-line drug for TB, shows that rifampin binds to the β-site on the RNAP and inhibits RNA synthesis by blocking the path of the elongating RNA, which is believed to be its mechanism of action [Campbell, et al., *Cell* 104, 901-912 (2001)]. However, there are other sites existing on TB RNAP that could be targeted by inhibitors to interfere with this RNAP's functional mechanism. For example, there is a pocket on the TB RNAP catalytic core domain that contains a structural region that bears some resemblance to the catalytic triad area of the catalytic core domain of HIV-1 integrase [Frankel, et al., *Annu. Rev. Biochem.* 67, 1-25 (1998), Cox and Nair, *Antimicrob. Agents Chemother.* 17, 343-353 (2006)]. This is the β'-site of this RNAP, which is close to 18 Å away from the binding location of rifampin in the β-site. Computational chemical biology and molecular modeling experiments revealed that our novel anti-TB compounds described in this invention are capable of binding inside the catalytic channel of the RNAP β'-pocket, interacting with a $Mg^{2+}$ ion and a number of other residues in the β'-pocket, as well as with a few residues that are in the structural region that forms the interface between β'- and β-pockets. Our compounds appear to bind to the TB RNAP holoenzyme either before or after binding of the promoter DNA, which produces obstruction of transcription, resulting in failure of RNAP catalysis to initiate transcription. It is relevant to state that our compounds are not alternate substrates or transition state mimics of the RNAP polymerization reaction.

The new class of compounds described in this invention are multifunctional and are designed with the following structural components: dibenzyl pyridinone scaffold, diketo-enolic functionality, and a piperazine carboxamide moiety that carries an aromatic or substituted aromatic group on the second piperazine nitrogen. The compounds have been designed as treatments for MDR-TB and have therapeutic applications in XDR-TB and XXDR-TB. An example is shown below (Figure 1). This compound is active against MDR-TB with a minimum inhibitory concentration (MIC, i.e., the lowest concentration to completely inhibit growth of MDR-TB) of <1 microgram/mL (Agar dilution susceptibility method). In addition, this compound exhibits significant in vitro anti-HIV activity in cell culture with $EC_{90}$ (concentration for 90% inhibition of virus replication) in the nM range.

Figure 1

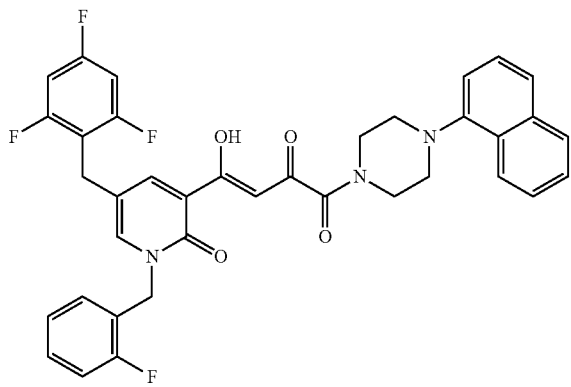

SUMMARY OF THE INVENTION

Multifunctional compounds that have a dibenzyl pyridinone scaffold, a diketo/enolic functionality, a piperazine carboxamide moiety, and a N-substituted aromatic or substituted aromatic group on the piperazine ring and methods for their preparation and use are disclosed. The compounds are represented by Formula I and include tautomers, geometric isomers, regioisomers and pharmaceutically acceptable salts thereof, wherein the pyridinone scaffold and R and X groups are as otherwise defined in the specification. These complex multifunctional compounds exhibit substantial activity as novel anti-TB agents. The compounds are useful in the prevention and/or reducing the likelihood, inhibition or treatment of infection by MDR-TB, with applications in XDR-TB and XXDR-TB, and in the treatment of drug-resistant TB where there is also co-infection with HIV, either as the compounds, or as pharmaceutically acceptable salts, with pharmaceutically acceptable carriers, used alone or in combination with other anti-TB agents, anti-AIDS compounds, other antivirals, anti-infectives, immunomodulators, antibiotics, vaccines, and other therapeutic agents, which can be used to create combination anti-TB cocktails. Methods of treating, preventing and/or reducing the likelihood of drug-resistant TB and methods of treating or preventing infection by drug-resistant TB are also described, the method comprising administering one or more compounds according to the present invention, optionally in combination with additional agents, including anti-HIV agents, in effective amounts to a patient or subject in need.

Compounds according to the present invention exhibit one or more of the following characteristics desired in anti-TB compounds: high efficacy against MDR-TB and other drug-resistant TB, low toxicity, favorable hydrophobicity, appropriate distribution of polar surface area, enhanced stability to metabolic degradation and a favorable drug-drug interaction profile. The present compounds represent a material advance in the treatment and/or prevention of MDR-TB or other drug-resistant TB and related secondary conditions and/or disease states or accompanying co-infections with HIV.

Pharmaceutical compositions which include one or more compounds according to the present invention in combination with a pharmaceutically acceptable carrier, additive or excipient, optionally in combination with at least one additional agent as otherwise described herein represent an additional aspect of the invention. A kit comprising a pharmaceutical composition according to the present invention and instructions on how to administer the composition to a patient in need represent a further aspect of the invention.

DETAILED DESCRIPTION OF THE INVENTION

The following terms are used throughout the specification to describe the present invention. Unless otherwise indicated, a term used to describe the present invention shall be given its ordinary meaning as understood by those skilled in the art.

The term "compound", as used herein, unless otherwise indicated, refers to any specific chemical compound disclosed herein and includes tautomers and geometric isomers, as well as pharmaceutically acceptable salts thereof. Within its use in context, the term compound generally refers to a single chemically stable compound which can be administered to a patient or subject, but also may include other compounds such as tautomers and geometric isomers. The breadth of the term "compound" shall be construed within the context of the use of the term. It is noted that where a substituent should be present in context but is not specifically signified, it is understood that such substituent represents a hydrogen (H) atom.

The term "patient" or "subject" is used throughout the specification to describe an animal, generally a mammal and preferably a human, to whom treatment, including prophylactic treatment, with the compositions according to the present invention is provided. For treatment of those infections, conditions or disease states which are specific for a specific animal such as a human patient, the term patient refers to that specific animal.

The term "effective" is used herein, unless otherwise indicated, to describe an amount of a compound or composition or component which, in context, is used to produce or effect an intended result, whether that result relates to the treatment of a microbial, viral or other disease state, disorder or condition associated with TB or alternatively, is used to produce another compound, agent or composition. This term subsumes all other effective amount or effective concentration terms which are otherwise described in the present application.

The term "scaffold" is used to mean a dibenzyl pyridinone chemical structure. The dibenzyl group has $R_1$, $R_2$, $R_3$ and $R_4$ substituents which are as defined herein. The scaffold contains additional functionalities including a diketo-enol group and a substituted piperazine carboxamide moiety of which the X groups are as defined herein.

The term "minimum inhibitory concentration" is defined as the lowest concentration of an anti-mycobacterial compound that will inhibit completely the growth of the microorganism as visibly discerned after a delineated period.

The term "prevention" is used within context to mean "reducing the likelihood" of a condition or disease state from occurring as a consequence of administration or concurrent administration of one or more compounds or compositions according to the present invention, alone or in combination with another agent. Thus, the term prevention is used within the context of a qualitative measure and it is understood that the use of a compound according to the present invention to reduce the likelihood of an occurrence of a condition or disease state as otherwise described herein will not be absolute, but will reflect the ability of the compound to reduce the likelihood of the occurrence within a population of patients or subjects in need of such prevention.

The term "multi-drug resistant *Mycobacterium tuberculosis*," which is referred to with the acronym, MDR-TB, describes tuberculosis that is resistant to isoniazid and rifampin, the two drugs that are used commonly for drug-susceptible TB and with treatment-adherent TB patients.

The term "extensively drug-resistant *Mycobacterium tuberculosis*," which is referred to with the acronym, XDR-TB, describes MDR-TB that has also developed resistance to one or more of the injectable second line TB drugs (kanamycin, capreomycin or amikacin) and also to a fluoroquinolone drug. The term "extremely drug-resistant *Mycobacterium tuberculosis*," referred to as XXDR-TB, is TB that is resistant to both first line and second line TB drugs.

The term "human immunodeficiency virus" or "HIV" shall be used to describe human immunodeficiency viruses 1 and 2 (HIV-1 and HIV-2). The terms "ARC" and "AIDS" refer to syndromes of the immune system caused by the human immunodeficiency virus, which are characterized by susceptibility to certain diseases and T cell counts which are depressed compared to normal counts. HIV progresses from Category 1 (Asymptomatic HIV Disease) to Category 2 (ARC), to Category 3 (AIDS), with the severity of the disease.

The term "coadministration" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided preferably that effective concentrations of coadministered compounds or compositions are found in the subject at a given time. The term coadministration also encompasses, in certain instances, the serial administration of agents which are administered serially in a patient to produce an intended effect, regardless of the time of administration and concentration of agent found in the subject.

The term "independently" is used herein to indicate that a variable, which is independently applied, varies independently from application to application.

The present invention is directed to compounds of the general molecular Formula below, including tautomer, geometric isomer and pharmaceutically acceptable salts thereof. The groups labeled as A and B represent unsubstituted and fluoro-substituted phenyl rings, with substitutions from mono- through to tetra-substituted, involving the ortho, meta and para positions (with reference to the methylene group to which the phenyl group is bound), and combinations thereof. The groups attached to the piperazine ring nitrogen and labeled as X are aromatic groups which term includes heteroaromatic groups. The groups R and X are as otherwise described in the specification.

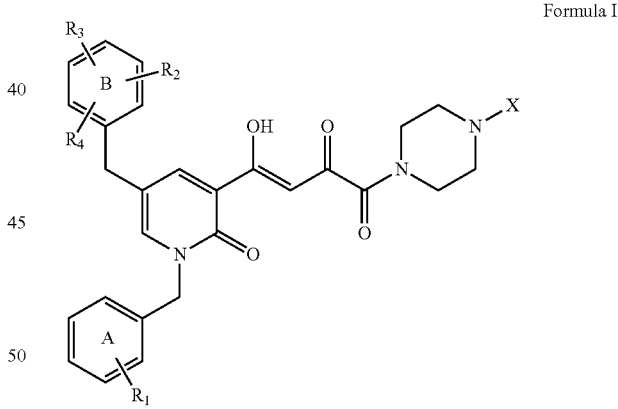

Formula I

Particular compounds of Formula I with respect to phenyl rings labeled A and B, which also carry the group X substitutions, include the following:

$R_1$=H, $R_2$=H, $R_3$=H, $R_4$=H
$R_1$=H, $R_2$=o-F, $R_3$=o-F, $R_4$=p-F
$R_1$=o-F, $R_2$=o-F, $R_3$=o-F, $R_4$=m-F
$R_1$=o-F, $R_2$=o-F, $R_3$=o-F, $R_4$=p-F
$R_1$=o-F, $R_2$=o-F, $R_3$=m-F, $R_4$=m-F
$R_1$=o-F, $R_2$=o-F, $R_3$=m-F, $R_4$=p-F
$R_1$=o-F, $R_2$=m-F, $R_3$=m-F, $R_4$=p-F
$R_1$=H, $R_2$=m-F, $R_3$=m-F, $R_4$=p-F
$R_1$=m-F, $R_2$=o-F, $R_3$=o-F, $R_4$=m-F
$R_1$=m-F, $R_2$=o-F, $R_3$=o-F, $R_4$=p-F
$R_1$=m-F, $R_2$=o-F, $R_3$=m-F, $R_4$=m-F $R_1$=m-F, $R_2$=o-F, $R_3$=m-F, $R_4$=p-F
$R_1$=m-F, $R_2$=m-F, $R_3$=m-F, $R_4$=p-F
$R_1$=H, $R_2$=o-F, $R_3$=o-F, $R_4$=m-F
$R_1$=p-F, $R_2$=o-F, $R_3$=o-F, $R_4$=m-F
$R_1$=p-F, $R_2$=o-F, $R_3$=o-F, $R_4$=p-F
$R_1$=p-F, $R_2$=o-F, $R_3$=m-F, $R_4$=m-F
$R_1$=p-F, $R_2$=o-F, $R_3$=m-F, $R_4$=p-F
$R_1$=p-F, $R_2$=m-F, $R_3$=m-F, $R_4$=p-F
$R_1$=o-F, $R_2$=m-F, $R_3$=m-F, $R_4$=H
$R_1$=o-F, $R_2$=p-F, $R_3$=H, $R_4$=H and
$R_1$=o-F, $R_2$=o-F, $R_3$=o-F, $R_4$=H By way of convention, o-F represents ortho substituted fluorine, m-F represents meta substituted fluorine and p-F represents para substituted fluorine.

Particular compounds of Formula I with respect to group X which are directed to optionally substituted aromatic groups, including heteroaryl groups, preferably include the following groups. These also carry the substitutions shown above in the rings A and B. These preferred X groups are as follows:

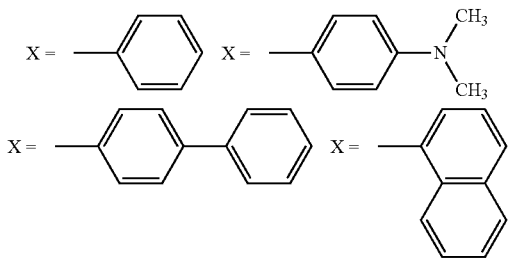

Also embraced by the present invention are pharmaceutical compositions useful for the treatment of MDR-TB, comprising an effective amount of at least one compound of this invention as described herein, and a pharmaceutically acceptable carrier, additive or excipient. Pharmaceutical compositions useful for treating infection by drug-resistant TB or for treating, in combination with other drugs, MDR-TB co-infections such as those with HIV, are included by the present invention. In addition, the present invention is directed to a pharmaceutical composition comprising, in effective combination, a therapeutically effective amount of at least one compound of the present invention and a suitable and effective combination with: (i) one or more other TB drugs, including drugs against resistant TB; (ii) a therapeutically effective amount of an agent(s) for the treatment of AIDS; (iii) an anti-infective agent, (iv) an immunomodulator, (v) other useful therapeutic agents, including antibiotics, vaccines and other antiviral agents.

Other applications are also part of this invention. For example, the compounds of this invention may also be useful for treatments of drug resistant forms of TB, including XDR-TB and XXDR-TB and in combination therapeutic treatment for these resistant TB infections as well as co-infections involving HIV and other viral infections.

The compounds of the present invention also embrace geometric isomers and these forms are also included in the present invention.

Tautomeric forms may also exist with compounds of the present invention. Thus, the terminology "and tautomers thereof" is used in describing tautomeric forms of compounds of Formula I such as Ia and Ib (shown below). By naming compounds as being represented by the general Formula I and tautomers thereof, it is understood that for the purposes of the present invention, that tautomers 1a and 1b are also included. Similarly, by referring to compound (1a), it is understood for the purposes of the present application that tautomers (1) and (1b) are also intended to be included. The same holds true for references to tautomer (1b).

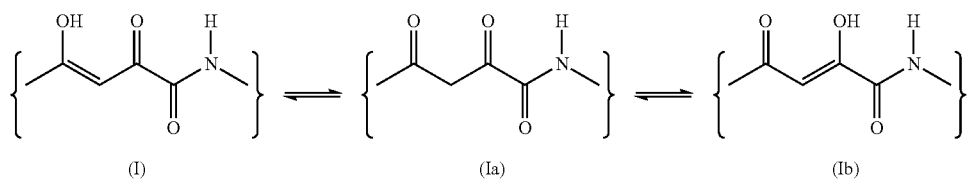

When the variables involving $R_1$, $R_2$, $R_3$, and $R_4$ occur more than once in any Formula I, the definition on each occurrence is independent of its definition at every other occurrence. Combinations of pyridinones and R and X variables are permissible only if, in context, such combinations result in stable compounds.

For the X groups, the term "aromatic," in context, refers to a substituted or unsubstituted aromatic group having a single ring (e.g., benzene) or multiple condensed rings (e.g., naphthyl, anthracenyl, phenanthryl).

Particular compounds of Formula I include:
1. 4-(1,5-dibenzyl-2-oxo-1,2-dihydropyridin-3-yl)-4-hydroxy-1-(4-phenylpiperazin-1-yl)but-3-ene-1,2-dione
2. 1-(4-([1,1'-biphenyl]-4-yl)piperazin-1-yl)-4-(1,5-dibenzyl-2-oxo-1,2-dihydropyridin-3-yl)-4-hydroxybut-3-ene-1,2-dione
3. 4-(1,5-dibenzyl-2-oxo-1,2-dihydropyridin-3-yl)-4-hydroxy-1-(4-(naphthalen-1-yl)piperazin-1-yl)but-3-ene-1,2-dione
4. 4-(1,5-dibenzyl-2-oxo-1,2-dihydropyridin-3-yl)-1-(4-(4-(dimethylamino)phenyl)piperazin-1-yl)-4-hydroxybut-3-ene-1,2-dione
5. 1-(4-(4-(1H-pyrrol-1-yl)phenyl)piperazin-1-yl)-4-(1,5-dibenzyl-2-oxo-1,2-dihydropyridin-3-yl)-4-hydroxybut-3-ene-1,2-dione -continued

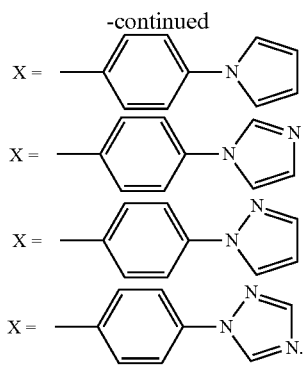

6. 1-(4-(4-(1H-imidazol-1-yl)phenyl)piperazin-1-yl)-4-(1,5-dibenzyl-2-oxo-1,2-dihydropyridin-3-yl)-4-hydroxybut-3-ene-1,2-dione
7. 1-(4-(4-(1H-pyrazol-1-yl)phenyl)piperazin-1-yl)-4-(1,5-dibenzyl-2-oxo-1,2-dihydropyridin-3-yl)-4-hydroxybut-3-ene-1,2-dione
8. 1-(4-(4-(1H-1,2,4-triazol-1-yl)phenyl)piperazin-1-yl)-4-(1,5-dibenzyl-2-oxo-1,2-dihydropyridin-3-yl)-4-hydroxybut-3-ene-1,2-dione
9. 4-(1-(2-fluorobenzyl)-5-(4-fluorobenzyl)-2-oxo-1,2-dihydropyridin-3-yl)-4-hydroxy-1-(4-phenylpiperazin-1-yl)but-3-ene-1,2-dione
10. 1-(4-([1,1'-biphenyl]-4-yl)piperazin-1-yl)-4-(1-(2-fluorobenzyl)-5-(4-fluorobenzyl)-2-oxo-1,2-dihydropyridin-3-yl)-4-hydroxybut-3-ene-1,2-dione
11. 4-(1-(2-fluorobenzyl)-5-(4-fluorobenzyl)-2-oxo-1,2-dihydropyridin-3-yl)-4-hydroxy-1-(4-(naphthalen-1-yl)piperazin-1-yl)but-3-ene-1,2-dione
12. 1-(4-(4-(dimethylamino)phenyl)piperazin-1-yl)-4-(1-(2-fluorobenzyl)-5-(4-fluorobenzyl)-2-oxo-1,2-dihydropyridin-3-yl)-4-hydroxybut-3-ene-1,2-dione
13. 1-(4-(4-(1H-pyrrol-1-yl)phenyl)piperazin-1-yl)-4-(1-(2-fluorobenzyl)-5-(4-fluorobenzyl)-2-oxo-1,2-dihydropyridin-3-yl)-4-hydroxybut-3-ene-1,2-dione
14. 1-(4-(4-(1H-imidazol-1-yl)phenyl)piperazin-1-yl)-4-(1-(2-fluorobenzyl)-5-(4-fluorobenzyl)-2-oxo-1,2-dihydropyridin-3-yl)-4-hydroxybut-3-ene-1,2-dione
15. 1-(4-(4-(1H-pyrazol-1-yl)phenyl)piperazin-1-yl)-4-(1-(2-fluorobenzyl)-5-(4-fluorobenzyl)-2-oxo-1,2-dihydropyridin-3-yl)-4-hydroxybut-3-ene-1,2-dione
16. 1-(4-(4-(1H-1,2,4-triazol-1-yl)phenyl)piperazin-1-yl)-4-(1-(2-fluorobenzyl)-5-(4-fluorobenzyl)-2-oxo-1,2-dihydropyridin-3-yl)-4-hydroxybut-3-ene-1,2-dione
17. 4-(5-(2,6-difluorobenzyl)-1-(2-fluorobenzyl)-2-oxo-1,2-dihydropyridin-3-yl)-4-hydroxy-1-(4-(naphthalen-1-yl)piperazin-1-yl)but-3-ene-1,2-dione
18. 4-(5-(2,6-difluorobenzyl)-1-(2-fluorobenzyl)-2-oxo-1,2-dihydropyridin-3-yl)-4-hydroxy-1-(4-phenylpiperazin-1-yl)but-3-ene-1,2-dione
19. 1-(4-([1,1'-biphenyl]-4-yl)piperazin-1-yl)-4-(5-(2,6-difluorobenzyl)-1-(2-fluorobenzyl)-2-oxo-1,2-dihydropyridin-3-yl)-4-hydroxybut-3-ene-1,2-dione
20. 4-(5-(2,6-difluorobenzyl)-1-(2-fluorobenzyl)-2-oxo-1,2-dihydropyridin-3-yl)-1-(4-(4-(dimethylamino)phenyl)piperazin-1-yl)-4-hydroxybut-3-ene-1,2-dione
21. 1-(4-(4-(1H-pyrrol-1-yl)phenyl)piperazin-1-yl)-4-(5-(2,6-difluorobenzyl)-1-(2-fluorobenzyl)-2-oxo-1,2-dihydropyridin-3-yl)-4-hydroxybut-3-ene-1,2-dione
22. 1-(4-(4-(1H-imidazol-1-yl)phenyl)piperazin-1-yl)-4-(5-(2,6-difluorobenzyl)-1-(2-fluorobenzyl)-2-oxo-1,2-dihydropyridin-3-yl)-4-hydroxybut-3-ene-1,2-dione
23. 1-(4-(4-(1H-pyrazol-1-yl)phenyl)piperazin-1-yl)-4-(5-(2,6-difluorobenzyl)-1-(2-fluorobenzyl)-2-oxo-1,2-dihydropyridin-3-yl)-4-hydroxybut-3-ene-1,2-dione
24. 1-(4-(4-(1H-1,2,4-triazol-1-yl)phenyl)piperazin-1-yl)-4-(5-(2,6-difluorobenzyl)-1-(2-fluorobenzyl)-2-oxo-1,2-dihydropyridin-3-yl)-4-hydroxybut-3-ene-1,2-dione
25. 4-(5-(3,5-difluorobenzyl)-1-(2-fluorobenzyl)-2-oxo-1,2-dihydropyridin-3-yl)-4-hydroxy-1-(4-phenylpiperazin-1-yl)but-3-ene-1,2-dione
26. 1-(4-([1,1'-biphenyl]-4-yl)piperazin-1-yl)-4-(5-(3,5-difluorobenzyl)-1-(2-fluorobenzyl)-2-oxo-1,2-dihydropyridin-3-yl)-4-hydroxybut-3-ene-1,2-dione
27. 4-(5-(3,5-difluorobenzyl)-1-(2-fluorobenzyl)-2-oxo-1,2-dihydropyridin-3-yl)-4-hydroxy-1-(4-(naphthalen-1-yl)piperazin-1-yl)but-3-ene-1,2-dione
28. 4-(5-(3,5-difluorobenzyl)-1-(2-fluorobenzyl)-2-oxo-1,2-dihydropyridin-3-yl)-1-(4-(4-(dimethylamino)phenyl)piperazin-1-yl)-4-hydroxybut-3-ene-1,2-dione
29. 1-(4-(4-(1H-pyrrol-1-yl)phenyl)piperazin-1-yl)-4-(5-(3,5-difluorobenzyl)-1-(2-fluorobenzyl)-2-oxo-1,2-dihydropyridin-3-yl)-4-hydroxybut-3-ene-1,2-dione
30. 1-(4-(4-(1H-imidazol-1-yl)phenyl)piperazin-1-yl)-4-(5-(3,5-difluorobenzyl)-1-(2-fluorobenzyl)-2-oxo-1,2-dihydropyridin-3-yl)-4-hydroxybut-3-ene-1,2-dione
31. 1-(4-(4-(1H-pyrazol-1-yl)phenyl)piperazin-1-yl)-4-(5-(3,5-difluorobenzyl)-1-(2-fluorobenzyl)-2-oxo-1,2-dihydropyridin-3-yl)-4-hydroxybut-3-ene-1,2-dione
32. 1-(4-(4-(1H-1,2,4-triazol-1-yl)phenyl)piperazin-1-yl)-4-(5-(3,5-difluorobenzyl)-1-(2-fluorobenzyl)-2-oxo-1,2-dihydropyridin-3-yl)-4-hydroxybut-3-ene-1,2-dione
33. 4-(1-benzyl-2-oxo-5-(2,4,6-trifluorobenzyl)-1,2-dihydropyridin-3-yl)-4-hydroxy-1-(4-phenylpiperazin-1-yl)but-3-ene-1,2-dione
34. 1-(4-([1,1'-biphenyl]-4-yl)piperazin-1-yl)-4-(1-benzyl-2-oxo-5-(2,4,6-trifluorobenzyl)-1,2-dihydropyridin-3-yl)-4-hydroxybut-3-ene-1,2-dione
35. 4-(1-benzyl-2-oxo-5-(2,4,6-trifluorobenzyl)-1,2-dihydropyridin-3-yl)-4-hydroxy-1-(4-(naphthalen-1-yl)piperazin-1-yl)but-3-ene-1,2-dione
36. 4-(1-benzyl-2-oxo-5-(2,4,6-trifluorobenzyl)-1,2-dihydropyridin-3-yl)-1-(4-(4-(dimethylamino)phenyl)piperazin-1-yl)-4-hydroxybut-3-ene-1,2-dione
37. 1-(4-(4-(1H-pyrrol-1-yl)phenyl)piperazin-1-yl)-4-(1-benzyl-2-oxo-5-(2,4,6-trifluorobenzyl)-1,2-dihydropyridin-3-yl)-4-hydroxybut-3-ene-1,2-dione
38. 1-(4-(4-(1H-imidazol-1-yl)phenyl)piperazin-1-yl)-4-(1-benzyl-2-oxo-5-(2,4,6-trifluorobenzyl)-1,2-dihydropyridin-3-yl)-4-hydroxybut-3-ene-1,2-dione
39. 1-(4-(4-(1H-pyrazol-1-yl)phenyl)piperazin-1-yl)-(4-(1-benzyl-2-oxo-5-(2,4,6-trifluorobenzyl)-1,2-dihydropyridin-3-yl)-4-hydroxybut-3-ene-1,2-dione
40. 1-(4-(4-(1H-1,2,4-triazol-1-yl)phenyl)piperazin-1-yl)-4-(1-benzyl-2-oxo-5-(2,4,6-trifluorobenzyl)-1,2-dihydropyridin-3-yl)-4-hydroxybut-3-ene-1,2-dione
41. 4-(1-(2-fluorobenzyl)-2-oxo-5-(2,4,6-trifluorobenzyl)-1,2-dihydropyridin-3-yl)-4-hydroxy-1-(4-phenylpiperazin-1-yl)but-3-ene-1,2-dione
42. 1-(4-([1,1'-biphenyl]-4-yl)piperazin-1-yl)-4-(1-(2-fluorobenzyl)-2-oxo-5-(2,4,6-trifluorobenzyl)-1,2-dihydropyridin-3-yl)-4-hydroxybut-3-ene-1,2-dione
43. 4-(1-(2-fluorobenzyl)-2-oxo-5-(2,4,6-trifluorobenzyl)-1,2-dihydropyridin-3-yl)-4-hydroxy-1-(4-(naphthalen-1-yl)piperazin-1-yl)but-3-ene-1,2-dione
44. 1-(4-(4-(dimethylamino)phenyl)piperazin-1-yl)-4-(1-(2-fluorobenzyl)-2-oxo-5-(2,4,6-trifluorobenzyl)-1,2-dihydropyridin-3-yl)-4-hydroxybut-3-ene-1,2-dione
45. 1-(4-(4-(1H-pyrrol-1-yl)phenyl)piperazin-1-yl)-4-(1-(2-fluorobenzyl)-2-oxo-5-(2,4,6-trifluorobenzyl)-1,2-dihydropyridin-3-yl)-4-hydroxybut-3-ene-1,2-dione
46. 1-(4-(4-(1H-imidazol-1-yl)phenyl)piperazin-1-yl)-4-(1-(2-fluorobenzyl)-2-oxo-5-(2,4,6-trifluorobenzyl)-1,2-dihydropyridin-3-yl)-4-hydroxybut-3-ene-1,2-dione
47. 1-(4-(4-(1H-pyrazol-1-yl)phenyl)piperazin-1-yl)-4-(1-(2-fluorobenzyl)-2-oxo-5-(2,4,6-trifluorobenzyl)-1,2-dihydropyridin-3-yl)-4-hydroxybut-3-ene-1,2-dione
48. 1-(4-(4-(1H-1,2,4-triazol-1-yl)phenyl)piperazin-1-yl)-4-(1-(2-fluorobenzyl)-2-oxo-5-(2,4,6-trifluorobenzyl)-1,2-dihydropyridin-3-yl)-4-hydroxybut-3-ene-1,2-dione
49. 4-(1-(4-fluorobenzyl)-2-oxo-5-(2,4,6-trifluorobenzyl)-1,2-dihydropyridin-3-yl)-4-hydroxy-1-(4-phenylpiperazin-1-yl)but-3-ene-1,2-dione 50. 1-(4-([1,1'-biphenyl]-4-yl)piperazin-1-yl)-4-(1-(4-fluorobenzyl)-2-oxo-5-(2,4,6-trifluorobenzyl)-1,2-dihydropyridin-3-yl)-4-hydroxybut-3-ene-1,2-dione
51. 4-(1-(4-fluorobenzyl)-2-oxo-5-(2,4,6-trifluorobenzyl)-1,2-dihydropyridin-3-yl)-4-hydroxy-1-(4-(15naphthalen-1-yl)piperazin-1-yl)but-3-ene-1,2-dione
52. 1-(4-(4-(dimethylamino)phenyl)piperazin-1-yl)-4-(1-(4-fluorobenzyl)-2-oxo-5-(2,4,6-trifluorobenzyl)-1,2-dihydropyridin-3-yl)-4-hydroxybut-3-ene-1,2-dione
53. 1-(4-(4-(1H-pyrrol-1-yl)phenyl)piperazin-1-yl)-4-(1-(4-fluorobenzyl)-2-oxo-5-(2,4,6-trifluorobenzyl)-1,2-dihydropyridin-3-yl)-4-hydroxybut-3-ene-1,2-dione
54. 1-(4-(4-(1H-imidazol-1-yl)phenyl)piperazin-1-yl)-4-(1-(4-fluorobenzyl)-2-oxo-5-(2,4,6-trifluorobenzyl)-1,2-dihydropyridin-3-yl)-4-hydroxybut-3-ene-1,2-dione
55. 1-(4-(4-(1H-pyrazol-1-yl)phenyl)piperazin-1-yl)-4-(1-(4-fluorobenzyl)-2-oxo-5-(2,4,6-trifluorobenzyl)-1,2-dihydropyridin-3-yl)-4-hydroxybut-3-ene-1,2-dione
56. 1-(4-(4-(1H-1,2,4-triazol-1-yl)phenyl)piperazin-1-yl)-4-(1-(4-fluorobenzyl)-2-oxo-5-(2,4,6-trifluorobenzyl)-1,2-dihydropyridin-3-yl)-4-hydroxybut-3-ene-1,2-dione
57. 4-(1-(2-fluorobenzyl)-2-oxo-5-(2,3,6-trifluorobenzyl)-1,2-dihydropyridin-3-yl)-4-hydroxy-1-(4-phenylpiperazin-1-yl)but-3-ene-1,2-dione
58. 1-(4-([1,1'-biphenyl]-4-yl)piperazin-1-yl)-4-(1-(2-fluorobenzyl)-2-oxo-5-(2,3,6-trifluorobenzyl)-1,2-dihydropyridin-3-yl)-4-hydroxybut-3-ene-1,2-dione
59. 4-(1-(2-fluorobenzyl)-2-oxo-5-(2,3,6-trifluorobenzyl)-1,2-dihydropyridin-3-yl)-4-hydroxy-1-(4-(naphthalen-1-yl)piperazin-1-yl)but-3-ene-1,2-dione
60. 1-(4-(4-(dimethylamino)phenyl)piperazin-1-yl)-4-(1-(2-fluorobenzyl)-2-oxo-5-(2,3,6-trifluorobenzyl)-1,2-dihydropyridin-3-yl)-4-hydroxybut-3-ene-1,2-dione
61. 1-(4-(4-(1H-pyrrol-1-yl)phenyl)piperazin-1-yl)-4-(1-(2-fluorobenzyl)-2-oxo-5-(2,3,6-trifluorobenzyl)-1,2-dihydropyridin-3-yl)-4-hydroxybut-3-ene-1,2-dione
62. 1-(4-(4-(1H-imidazol-1-yl)phenyl)piperazin-1-yl)-4-(1-(2-fluorobenzyl)-2-oxo-5-(2,3,6-trifluorobenzyl)-1,2-dihydropyridin-3-yl)-4-hydroxybut-3-ene-1,2-dione
63. 1-(4-(4-(1H-pyrazol-1-yl)phenyl)piperazin-1-yl)-4-(1-(2-fluorobenzyl)-2-oxo-5-(2,3,6-trifluorobenzyl)-1,2-dihydropyridin-3-yl)-4-hydroxybut-3-ene-1,2-dione
64. 1-(4-(4-(1H-1,2,4-triazol-1-yl)phenyl)piperazin-1-yl)-4-(1-(2-fluorobenzyl)-2-oxo-5-(2,3,6-trifluorobenzyl)-1,2-dihydropyridin-3-yl)-4-hydroxybut-3-ene-1,2-dione
65. 4-(1-(2-fluorobenzyl)-2-oxo-5-(2,3,5-trifluorobenzyl)-1,2-dihydropyridin-3-yl)-4-hydroxy-1-(4-phenylpiperazin-1-yl)but-3-ene-1,2-dione
66. 1-(4-([1,1'-biphenyl]-4-yl)piperazin-1-yl)-4-(1-(2-fluorobenzyl)-2-oxo-5-(2,3,5-trifluorobenzyl)-1,2-dihydropyridin-3-yl)-4-hydroxybut-3-ene-1,2-dione
67. 4-(1-(2-fluorobenzyl)-2-oxo-5-(2,3,5-trifluorobenzyl)-1,2-dihydropyridin-3-yl)-4-hydroxy-1-(4-(naphthalen-1-yl)piperazin-1-yl)but-3-ene-1,2-dione
68. 1-(4-(4-(dimethylamino)phenyl)piperazin-1-yl)-4-(1-(2-fluorobenzyl)-2-oxo-5-(2,3,5-trifluorobenzyl)-1,2-dihydropyridin-3-yl)-4-hydroxybut-3-ene-1,2-dione
69. 1-(4-(4-(1H-pyrrol-1-yl)phenyl)piperazin-1-yl)-4-(1-(2-fluorobenzyl)-2-oxo-5-(2,3,5-trifluorobenzyl)-1,2-dihydropyridin-3-yl)-4-hydroxybut-3-ene-1,2-dione
70. 1-(4-(4-(1H-imidazol-1-yl)phenyl)piperazin-1-yl)-4-(1-(2-fluorobenzyl)-2-oxo-5-(2,3,5-trifluorobenzyl)-1,2-dihydropyridin-3-yl)-4-hydroxybut-3-ene-1,2-dione
71. 1-(4-(4-(1H-pyrazol-1-yl)phenyl)piperazin-1-yl)-4-(1-(2-fluorobenzyl)-2-oxo-5-(2,3,5-trifluorobenzyl)-1,2-dihydropyridin-3-yl)-4-hydroxybut-3-ene-1,2-dione
72. 1-(4-(4-(1H-1,2,4-triazol-1-yl)phenyl)piperazin-1-yl)-4-(1-(2-fluorobenzyl)-2-oxo-5-(2,3,5-trifluorobenzyl)-1,2-dihydropyridin-3-yl)-4-hydroxybut-3-ene-1,2-dione
73. 4-(1-(2-fluorobenzyl)-2-oxo-5-(2,3,4-trifluorobenzyl)-1,2-dihydropyridin-3-yl)-4-hydroxy-1-(4-phenylpiperazin-1-yl)but-3-ene-1,2-dione
74. 1-(4-([1,1'-biphenyl]-4-yl)piperazin-1-yl)-4-(1-(2-fluorobenzyl)-2-oxo-5-(2,3,4-trifluorobenzyl)-1,2-dihydropyridin-3-yl)-4-hydroxybut-3-ene-1,2-dione
75. 4-(1-(2-fluorobenzyl)-2-oxo-5-(2,3,4-trifluorobenzyl)-1,2-dihydropyridin-3-yl)-4-hydroxy-1-(4-(naphthalen-1-yl)piperazin-1-yl)but-3-ene-1,2-dione
76. 1-(4-(4-(dimethylamino)phenyl)piperazin-1-yl)-4-(1-(2-fluorobenzyl)-2-oxo-5-(2,3,4-trifluorobenzyl)-1,2-dihydropyridin-3-yl)-4-hydroxybut-3-ene-1,2-dione
77. 1-(4-(4-(1H-pyrrol-1-yl)phenyl)piperazin-1-yl)-4-(1-(2-fluorobenzyl)-2-oxo-5-(2,3,4-trifluorobenzyl)-1,2-dihydropyridin-3-yl)-4-hydroxybut-3-ene-1,2-dione
78. 1-(4-(4-(1H-imidazol-1-yl)phenyl)piperazin-1-yl)-4-(1-(2-fluorobenzyl)-2-oxo-5-(2,3,4-trifluorobenzyl)-1,2-dihydropyridin-3-yl)-4-hydroxybut-3-ene-1,2-dione
79. 1-(4-(4-(1H-pyrazol-1-yl)phenyl)piperazin-1-yl)-4-(1-(2-fluorobenzyl)-2-oxo-5-(2,3,4-trifluorobenzyl)-1,2-dihydropyridin-3-yl)-4-hydroxybut-3-ene-1,2-dione
80. 1-(4-(4-(1H-1,2,4-triazol-1-yl)phenyl)piperazin-1-yl)-4-(1-(2-fluorobenzyl)-2-oxo-5-(2,3,4-trifluorobenzyl)-1,2-dihydropyridin-3-yl)-4-hydroxybut-3-ene-1,2-dione
81. 4-(1-(2-fluorobenzyl)-2-oxo-5-(3,4,5-trifluorobenzyl)-1,2-dihydropyridin-3-yl)-4-hydroxy-1-(4-phenylpiperazin-1-yl)but-3-ene-1,2-dione
82. 1-(4-([1,1'-biphenyl]-4-yl)piperazin-1-yl)-4-(1-(2-fluorobenzyl)-2-oxo-5-(3,4,5-trifluorobenzyl)-1,2-dihydropyridin-3-yl)-4-hydroxybut-3-ene-1,2-dione
83. 4-(1-(2-fluorobenzyl)-2-oxo-5-(3,4,5-trifluorobenzyl)-1,2-dihydropyridin-3-yl)-4-hydroxy-1-(4-(naphthalen-1-yl)piperazin-1-yl)but-3-ene-1,2-dione
84. 1-(4-(4-(dimethylamino)phenyl)piperazin-1-yl)-4-(1-(2-fluorobenzyl)-2-oxo-5-(3,4,5-trifluorobenzyl)-1,2-dihydropyridin-3-yl)-4-hydroxybut-3-ene-1,2-dione
85. 1-(4-(4-(1H-pyrrol-1-yl)phenyl)piperazin-1-yl)-4-(1-(2-fluorobenzyl)-2-oxo-5-(3,4,5-trifluorobenzyl)-1,2-dihydropyridin-3-yl)-4-hydroxybut-3-ene-1,2-dione
86. 1-(4-(4-(1H-imidazol-1-yl)phenyl)piperazin-1-yl)-4-(1-(2-fluorobenzyl)-2-oxo-5-(3,4,5-trifluorobenzyl)-1,2-dihydropyridin-3-yl)-4-hydroxybut-3-ene-1,2-dione
87. 1-(4-(4-(1H-pyrazol-1-yl)phenyl)piperazin-1-yl)-4-(1-(2-fluorobenzyl)-2-oxo-5-(3,4,5-trifluorobenzyl)-1,2-dihydropyridin-3-yl)-4-hydroxybut-3-ene-1,2-dione
88. 1-(4-(4-(1H-1,2,4-triazol-1-yl)phenyl)piperazin-1-yl)-4-(1-(2-fluorobenzyl)-2-oxo-5-(3,4,5-trifluorobenzyl)-1,2-dihydropyridin-3-yl)-4-hydroxybut-3-ene-1,2-dione
89. 4-(1-benzyl-2-oxo-5-(3,4,5-trifluorobenzyl)-1,2-dihydropyridin-3-yl)-4-hydroxy-1-(4-phenylpiperazin-1-yl)but-3-ene-1,2-dione
90. 1-(4-([1,1'-biphenyl]-4-yl)piperazin-1-yl)-4-(1-benzyl-2-oxo-5-(3,4,5-trifluorobenzyl)-1,2-dihydropyridin-3-yl)-4-hydroxybut-3-ene-1,2-dione
91. 4-(1-benzyl-2-oxo-5-(3,4,5-trifluorobenzyl)-1,2-dihydropyridin-3-yl)-4-hydroxy-1-(4-(naphthalen-1-yl)piperazin-1-yl)but-3-ene-1,2-dione
92. 4-(1-benzyl-2-oxo-5-(3,4,5-trifluorobenzyl)-1,2-dihydropyridin-3-yl)-1-(4-(4-(dimethylamino)phenyl)piperazin-1-yl)-4-hydroxybut-3-ene-1,2-dione
93. 1-(4-(4-(1H-pyrrol-1-yl)phenyl)piperazin-1-yl)-4-(1-benzyl-2-oxo-5-(3,4,5-trifluorobenzyl)-1,2-dihydropyridin-3-yl)-4-hydroxybut-3-ene-1,2-dione 94. 1-(4-(4-(1H-imidazol-1-yl)phenyl)piperazin-1-yl)-4-(1-benzyl-2-oxo-5-(3,4,5-trifluorobenzyl)-1,2-dihydropyridin-3-yl)-4-hydroxybut-3-ene-1,2-dione
95. 1-(4-(4-(1H-pyrazol-1-yl)phenyl)piperazin-1-yl)-4-(1-benzyl-2-oxo-5-(3,4,5-trifluorobenzyl)-1,2-dihydropyridin-3-yl)-4-hydroxybut-3-ene-1,2-dione
96. 1-(4-(4-(1H-1,2,4-triazol-1-yl)phenyl)piperazin-1-yl)-4-(1-benzyl-2-oxo-5-(3,4,5-trifluorobenzyl)-1,2-dihydropyridin-3-yl)-4-hydroxybut-3-ene-1,2-dione
97. 4-(1-(3-fluorobenzyl)-2-oxo-5-(2,3,6-trifluorobenzyl)-1,2-dihydropyridin-3-yl)-4-hydroxy-1-(4-phenylpiperazin-1-yl)but-3-ene-1,2-dione
98. 1-(4-([1,1'-biphenyl]-4-yl)piperazin-1-yl)-4-(1-(3-fluorobenzyl)-2-oxo-5-(2,3,6-trifluorobenzyl)-1,2-dihydropyridin-3-yl)-4-hydroxybut-3-ene-1,2-dione
99. 4-(1-(3-fluorobenzyl)-2-oxo-5-(2,3,6-trifluorobenzyl)-1,2-dihydropyridin-3-yl)-4-hydroxy-1-(4-(naphthalene-1-yl)piperazin-1-yl)but-3-ene-1,2-dione
100. 1-(4-(4-(dimethylamino)phenyl)piperazin-1-yl)-4-(1-(3-fluorobenzyl)-2-oxo-5-(2,3,6-trifluorobenzyl)-1,2-dihydropyridin-3-yl)-4-hydroxybut-3-ene-1,2-dione
101. 1-(4-(4-(1H-pyrrol-1-yl)phenyl)piperazin-1-yl)-4-(1-(3-fluorobenzyl)-2-oxo-5-(2,3,6-trifluorobenzyl)-1,2-dihydropyridin-3-yl)-4-hydroxybut-3-ene-1,2-dione
102. 1-(4-(4-(1H-imidazol-1-yl)phenyl)piperazin-1-yl)-4-(1-(3-fluorobenzyl)-2-oxo-5-(2,3,6-trifluorobenzyl)-1,2-dihydropyridin-3-yl)-4-hydroxybut-3-ene-1,2-dione
103. 1-(4-(4-(1H-pyrazol-1-yl)phenyl)piperazin-1-yl)-4-(1-(3-fluorobenzyl)-2-oxo-5-(2,3,6-trifluorobenzyl)-1,2-dihydropyridin-3-yl)-4-hydroxybut-3-ene-1,2-dione
104. 1-(4-(4-(1H-1,2,4-triazol-1-yl)phenyl)piperazin-1-yl)-4-(1-(3-fluorobenzyl)-2-oxo-5-(2,3,6-trifluorobenzyl)-1,2-dihydropyridin-3-yl)-4-hydroxybut-3-ene-1,2-dione
105. 4-(1-(3-fluorobenzyl)-2-oxo-5-(2,4,6-trifluorobenzyl)-1,2-dihydropyridin-3-yl)-4-hydroxy-1-(4-phenylpiperazin-1-yl)but-3-ene-1,2-dione
106. 1-(4-([1,1'-biphenyl]-4-yl)piperazin-1-yl)-4-(1-(3-fluorobenzyl)-2-oxo-5-(2,4,6-trifluorobenzyl)-1,2-dihydropyridin-3-yl)-4-hydroxybut-3-ene-1,2-dione
107. 4-(1-(3-fluorobenzyl)-2-oxo-5-(2,4,6-trifluorobenzyl)-1,2-dihydropyridin-3-yl)-4-hydroxy-1-(4-(naphthalene-1-yl)piperazin-1-yl)but-3-ene-1,2-dione
108. 1-(4-(4-(dimethylamino)phenyl)piperazin-1-yl)-4-(1-(3-fluorobenzyl)-2-oxo-5-(2,4,6-trifluorobenzyl)-1,2-dihydropyridin-3-yl)-4-hydroxybut-3-ene-1,2-dione
109. 1-(4-(4-(1H-pyrrol-1-yl)phenyl)piperazin-1-yl)-4-(1-(3-fluorobenzyl)-2-oxo-5-(2,4,6-trifluorobenzyl)-1,2-dihydropyridin-3-yl)-4-hydroxybut-3-ene-1,2-dione
110. 1-(4-(4-(1H-imidazol-1-yl)phenyl)piperazin-1-yl)-4-(1-(3-fluorobenzyl)-2-oxo-5-(2,4,6-trifluorobenzyl)-1,2-dihydropyridin-3-yl)-4-hydroxybut-3-ene-1,2-dione
111. 1-(4-(4-(1H-pyrazol-1-yl)phenyl)piperazin-1-yl)-4-(1-(3-fluorobenzyl)-2-oxo-5-(2,4,6-trifluorobenzyl)-1,2-dihydropyridin-3-yl)-4-hydroxybut-3-ene-1,2-dione
112. 1-(4-(4-(1H-1,2,4-triazol-1-yl)phenyl)piperazin-1-yl)-4-(1-(3-fluorobenzyl)-2-oxo-5-(2,4,6-trifluorobenzyl)-1,2-dihydropyridin-3-yl)-4-hydroxybut-3-ene-1,2-dione
113. 4-(1-(3-fluorobenzyl)-2-oxo-5-(2,3,5-trifluorobenzyl)-1,2-dihydropyridin-3-yl)-4-hydroxy-1-(4-phenylpiperazin-1-yl)but-3-ene-1,2-dione
114. 1-(4-([1,1'-biphenyl]-4-yl)piperazin-1-yl)-4-(1-(3-fluorobenzyl)-2-oxo-5-(2,3,5-trifluorobenzyl)-1,2-dihydropyridin-3-yl)-4-hydroxybut-3-ene-1,2-dione
115. 1-(4-(4-(dimethylamino)phenyl)piperazin-1-yl)-4-(1-(3-fluorobenzyl)-2-oxo-5-(2,3,5-trifluorobenzyl)-1,2-dihydropyridin-3-yl)-4-hydroxybut-3-ene-1,2-dione
116. 4-(1-(3-fluorobenzyl)-2-oxo-5-(2,3,5-trifluorobenzyl)-1,2-dihydropyridin-3-yl)-4-hydroxy-1-(4-(naphthalen-1-yl)piperazin-1-yl)but-3-ene-1,2-dione
117. 1-(4-(4-(1H-pyrrol-1-yl)phenyl)piperazin-1-yl)-4-(1-(3-fluorobenzyl)-2-oxo-5-(2,3,5-trifluorobenzyl)-1,2-dihydropyridin-3-yl)-4-hydroxybut-3-ene-1,2-dione
118. 1-(4-(4-(1H-imidazol-1-yl)phenyl)piperazin-1-yl)-4-(1-(3-fluorobenzyl)-2-oxo-5-(2,3,5-trifluorobenzyl)-1,2-dihydropyridin-3-yl)-4-hydroxybut-3-ene-1,2-dione
119. 1-(4-(4-(1H-pyrazol-1-yl)phenyl)piperazin-1-yl)-4-(1-(3-fluorobenzyl)-2-oxo-5-(2,3,5-trifluorobenzyl)-1,2-dihydropyridin-3-yl)-4-hydroxybut-3-ene-1,2-dione
120. 1-(4-(4-(1H-1,2,4-triazol-1-yl)phenyl)piperazin-1-yl)-4-(1-(3-fluorobenzyl)-2-oxo-5-(2,3,5-trifluorobenzyl)-1,2-dihydropyridin-3-yl)-4-hydroxybut-3-ene-1,2-dione
121. 4-(1-(3-fluorobenzyl)-2-oxo-5-(2,3,4-trifluorobenzyl)-1,2-dihydropyridin-3-yl)-4-hydroxy-1-(4-phenylpiperazin-1-yl)but-3-ene-1,2-dione
122. 1-(4-([1,1'-biphenyl]-4-yl)piperazin-1-yl)-4-(1-(3-fluorobenzyl)-2-oxo-5-(2,3,4-trifluorobenzyl)-1,2-dihydropyridin-3-yl)-4-hydroxybut-3-ene-1,2-dione
123. 4-(1-(3-fluorobenzyl)-2-oxo-5-(2,3,4-trifluorobenzyl)-1,2-dihydropyridin-3-yl)-4-hydroxy-1-(4-(naphthalen-1-yl)piperazin-1-yl)but-3-ene-1,2-dione
124. 1-(4-(4-(dimethylamino)phenyl)piperazin-1-yl)-4-(1-(3-fluorobenzyl)-2-oxo-5-(2,3,4-trifluorobenzyl)-1,2-dihydropyridin-3-yl)-4-hydroxybut-3-ene-1,2-dione
125. 1-(4-(4-(1H-pyrrol-1-yl)phenyl)piperazin-1-yl)-4-(1-(3-fluorobenzyl)-2-oxo-5-(2,3,4-trifluorobenzyl)-1,2-dihydropyridin-3-yl)-4-hydroxybut-3-ene-1,2-dione
126. 1-(4-(4-(1H-imidazol-1-yl)phenyl)piperazin-1-yl)-4-(1-(3-fluorobenzyl)-2-oxo-5-(2,3,4-trifluorobenzyl)-1,2-dihydropyridin-3-yl)-4-hydroxybut-3-ene-1,2-dione
127. 1-(4-(4-(1H-pyrazol-1-yl)phenyl)piperazin-1-yl)-4-(1-(3-fluorobenzyl)-2-oxo-5-(2,3,4-trifluorobenzyl)-1,2-dihydropyridin-3-yl)-4-hydroxybut-3-ene-1,2-dione
128. 1-(4-(4-(1H-1,2,4-triazol-1-yl)phenyl)piperazin-1-yl)-4-(1-(3-fluorobenzyl)-2-oxo-5-(2,3,4-trifluorobenzyl)-1,2-dihydropyridin-3-yl)-4-hydroxybut-3-ene-1,2-dione Therapeutically effective amounts of the compounds of the present invention may be administered to patients orally, including buccally, parenterally, by inhalation spray, topically, or rectally, in dosage unit formulations containing pharmaceutically-acceptable carriers, adjuvants and vehicles including nanoparticle drug delivery approaches. The term "pharmaceutically acceptable" is meant to infer that the carrier, diluent, excipient or other additive is biologically compatible with the other ingredients of the formulation and not deleterious to the patient or recipient. Pharmaceutical compositions are in pharmaceutical dosage form and may be administered in the form of orally-administrable suspensions or tablets, nasal sprays and injectable preparations (injectable aqueous or oleagenous suspensions or suppositories). This method of treatment is part of the invention. The administration approaches used (e.g., orally as solution or suspension, immediate release tablets, nasal aerosol or inhalation, injectable solutions or suspensions or rectally administered in the form of suppositories) involve techniques that are well-known in the art of pharmaceutical formulation.

The compounds of this invention can be administered orally to humans in a preferred form (such as tablets) and in an effective amount within a preferred dosage range. The specific dose level and frequency of dosage for any particular patient may be varied and will depend upon a variety of factors including compound activity, compound metabolism and duration of action, patient age, body weight, general health, sex, diet, mode and time of administration, rate of excretion, drug combination, the severity of the particular condition, and the condition of the patient undergoing therapy.

The present invention also includes therapeutically effective combinations of compounds of formula I with one or more other therapeutic agents such as other anti-TB drugs, AIDS antivirals, other antiviral agents, immunomodulators, anti-infectives, antibiotics, vaccines or other therapeutic agents. Some examples are given below.

Anti-TB Drugs, Antiviral Agents, Anti-Infectives, Immunomodulators, Opportunistic Infection Drugs, Other Relevant Drugs TB Treatments and TB Co-Infections

| Drug Name | Manufacturer Examples | Therapeutic Use |
| --- | --- | --- |
| Rifampin (Rifadin, Rimactane) | Sanofi Aventis LLC US | TB and TB-related mycobacterial infections |
| Rifapentine | Sanofi Aventis LLC US | TB |
| Isoniazid (Nydrazid) | Bristol Myers Squibb Eli Lilly Hoffmann La Roche Inc. Novartis Sandoz Inc. | TB |
| Ethambutol | Barr laboratories Inc. STI Pharma LLC West ward pharmaceutical corp. | Adjunct, in the treatment TB |
| Ethionamide | Wyeth Inc. | TB |
| Para-aminosalicylic acid (PAS) | Bristol Myers Squibb Co. | TB |
| Capreomycin | Akorn Inc. | Treatment of TB in combination with other drugs. |
| Amikacin | Abbott | *Mycobacterium avium* and M. tb. |
| Rifabutin (Mycobutin) | Pharmacia | Disseminated *Mycobacterium avium* complex (MAC) disease in patients with advanced HIV infection. |
| Streptomycin | Eli Lilly, Pfizer | TB |
| Pyrazinamide | Dava Inc., Mikart Inc. | Initial treatment of active TB in adults and children when combined with other TB agents |
| Cycloserine | Purdue GMP Center LLC, Chao Center Industrial pharmacy | Used in combination with other drugs to treat *Mycobacterium avium* complex (MAC) and TB. |
| Ciprofloxacin | Bayer, Teva, Baxter, Ranbaxy, Sandoz Inc. | TB and other infections caused by susceptible organisms. |
| Ofloxacin | Ortho McNeil, Sandoz Inc., Ranbaxy, Teva | TB and accompanying infections. |
| Levofloxacin | Ortho McNeil | TB and accompanying infections. |
| Clofazimine | Novartis | TB |
| Bedaquiline | Johnson & Johnson | Multidrug-resistant TB (MDR TB) |
| 097 | Hoechst/Bayer | HIV infection, AIDS, ARC (NNRT inhibitor) |
| Amprenivir 141W94, GWI41 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL HIV positive, AIDS |
| Alpha Interferon | Glaxo Wellcome | Kaposi's sarcoma, HIV in combination w/Retrovir |
| Ansamycin LM427 | Adria Laboratories (Dublin, OH) Erbamont (Stamford, CT) | ARC |

-continued

| Drug Name | Manufacturer Examples | Therapeutic Use |
|---|---|---|
| Antibody which neutralizes pH labile alpha aberrant Interferon | Advanced Biotherapy Concepts (Rockville, MD) | AIDS, ARC |
| AR 177 | Aronex Pharm | HIV infection, AIDS, ARC |
| Beta-fluoro-ddA | National Cancer Institute | AIDS-associated diseases |
| BMS-232623, (CGP-73547) | Bristol-Myers Squibb/Novartis | HIV infection, AIDS, ARC (protease inhibitor) |
| BMS-234475 (CGP-61755) | Bristol-Myers Squibb/Novartis | HIV infection, AIDS, ARC (protease inhibitor) |
| CI-1012 | Warner-Lambert | HIV-1 infection |
| Cidofovir | Gilead Science | CMV retinitis, herpes, Papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV Peripheral CMV Retinitis |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP-266) | DuPont Merck | HIV infection, AIDS, ARC (non-nucleoside RT Inhibitor |
| EL10 | Elan Corp, PLC (Gainesville, GA) | HIV infection |
| Famciclovir | Smith Kline | Herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive; combination with AZT/ddI/ddC |
| Isentress (Raltegravir) | Merck | HIV infection, AIDS, ARC (integrase inhibitor) |
| ISIS-2922 | ISIS Pharmaceuticals | CMV retinitis |
| KNI-272 | Natl. Cancer Institute | HIV-associated diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OR) | HIV inhibitor |
| Peptide T Octapeptide Sequence | Peninsula Labs (Belmont, CA) | AIDS |
| Trisodium Phosphonoformate. | Astra Pharm. Products Inc, | CVV retinitis, HIV infection, other CMV |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |

-continued

| Drug Name | Manufacturer Examples | Therapeutic Use |
| --- | --- | --- |
| Ritonavir | Abbott | HIV infection, AIDS, ARC (protease inhibitor) |
| Saquinavir | Roffmann-LaRoche | HIV infection, AIDS, ARC (protease inhibitor) |
| Stavudine; d4T Didehydrodeoxythymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | Asymptomatic HIV positive, LAS, ARC |
| VX-478 | Vertex | HIV infection, AIDS, ARC |
| Zalcitabine | Hoffmann-LaRoche | HIV infection, AIDS, ARCwithAZT |
| Zidovudine; AZT | Glaxo Wellcome | HIV infection, AIDS, ARC, Kaposi's sarcoma, in combination with other therapies |
| Tenofovir diisoproxil fumarate salt (Viread ®) | Gilead | HIV infection, AIDS, (RT inhibitor) |
| Combivir ® | GSK | HIV infection, AIDS, (RT inhibitor) |
| Abacavir succinate (or Ziagen ®) | GSK | HIV infection, AIDS, (reverse transcriptase inhibitor) |
| Fuzeon ® (or T-20) | Roche/Trimeris | HIV infection, AIDS, viral Fusion inhibitor |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki Immuno PHARM | Blocks HIV fusion with CD4 + cells |
| Gamma Interferon | Genentech | ARC, in combination w/TNF |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 1mmunex | Hoffman-LaRoche | AIDS, ARC, HIV, in combination w/AZT |
| IL-2 Interleukin-2 (aldeslukin) | Chiron | AIDS, increase in CD4 cell counts |
| Immune Globulin (human) | Cutter Biological Intravenous (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |

-continued

| Drug Name | Manufacturer Examples | Therapeutic Use |
|---|---|---|
| Remune | Immune Response Corp. | Immunotherapeutic |
| rCD4 Recombinant Soluble Human CD4-IgG | Genentech | AIDS, ARC |
| rCD4-IgG Hybrids | | AIDS, ARC |
| Recombinant Soluble HumanCD4 | Biogen | AIDS, ARC |
| Interferon Alfa 2a | Hoffman-LaRoche | Kaposi's sarcoma, AIDS, AR, combination w/AZT |
| SK&F1-6528 Soluble T4 | Smith Kline | HIV infection |
| Thymopentin | Immunobiology Research Institute (Annandale, NJ) | HIV infection |
| Tumor Necrosis Factor (TNF) | Genentech | ARC, in combination w/gamma Interferon |
| AK602 | Kumamoto University Japan | HIV infection (entry and fusion inhibitor) |
| Alovudine | Medivir, UK Ltd. | HIV infection (nucleoside RT inhibitor) |
| Amdoxovir | RFS Pharma, LLC | Treatment of HIV and HBV infections (nucleoside RT Inhibitor) |
| AMD070 | AnorMED, Inc. | HIV infection (entry and fusion inhibitor) |
| Atazanavir (Reyataz) | Bristol-Myers Squibb | HIV infection (protease inhibitor) |
| AVX754 (apricitabine) | Avexa Ltd. | HIV infection (nucleoside RT inhibitor) |
| Bevirimat | Panacos Pharmaceuticals | HIV infection (maturation inhibitor) |
| BI-201 | BioInvent | HIV infection (gene therapy, blocks HIV tat gene). |
| BMS-378806 | Bristol-Myers Squibb | HIV infection (entry inhibitor) |
| BMS-488043 | Bristol-Myers Squibb | HIV infection (entry and fusion inhibitor) |
| BMS-707035 | Bristol-Myers Squibb | HIV infection (integase inhibitor) |
| C31G | Cellegy Inc. | Pharmaceuticals, HIV infection and other sexually transmitted diseases (STDs) |
| Carbopol 974P | ReProtect, LLC | Sexual transmission of HIV |
| Calanolide A | Sarawak MediChem Pharmaceuticals, Inc. | HIV infection (non-nucleoside RT inhibitor) |
| Carrageenan | FMC Biopolymer | HIV microbicide |
| Cellulose sulfate | Polydex Pharmaceuticals, Ltd. | Prevention of HIV infection and other sexually transmitted diseases |
| Cyanovirin-N | Cellegy Pharmaceuticals, Inc. | Prevention of sexual transmission of HIV infection |
| Darunavir | Tibotec | HIV infection (coadministered with ritonavir) |
| Delavirdine | Pfizer | HIV infection (nonnucleoside RT inhibitor) |
| Dextran sulfate | Ueno Fine Chemicals Industry, Ltd. | Prevention of transmission of HIV |
| Didanosine (Videx, Videx EC) | Bristol-Myers Squibb | HIV infection (nucleoside RT inhibitor) |
| Efavirenz | Bristol-Myers Squibb | HIV infection (nonnucleoside RT inhibitor) |
| Elvucitabine | Achillion Pharmaceuticals | HIV infection (nucleoside RT inhibitor) |
| Emtricitabine | Gilead Sciences | HIV infection (nucleoside RT inhibitor) |
| Fosamprenavir (Lexiva) | GlaxoSmithKline | HIV infection (protease inhibitor) |

-continued

| Drug Name | Manufacturer Examples | Therapeutic Use |
|---|---|---|
| Fozivudine tidoxil | Heidelberg Pharma | HIV infection (entry and fusion inhibitor) |
| Elvitegravir | Gilead Sciences | HIV infection (integase inhibitor) |
| GSK-873, 140 (aplaviroc) | GlaxoSmithKline | HIV infection (entry and fusion inhibitor) |
| GSK-364735 | Glaxo SmithKline | HIV infection (integase inhibitor) |
| GW640385 (brecanavir) | GlaxoSmithKline | HIV infection (protease inhibitor) |
| HG0004 | Human Genome Sciences | HIV infection (entry and fusion inhibitor) |
| HGTV43 | Enzo Therapeutics | HIV infection (antisense drug) |
| Hydroxyethyl cellulose | Union Carbide | Prevent sexual transmission of HIV |
| INCB9471 | Incyte Corporation | HIV infection (entry and fusion inhibitor) |
| KP-1461 | Koronis Pharmaceuticals | HIV infection (nucleoside RT inhibitor) |
| Lopinavir | Abbott Laboratories | HIV infection (protease inhibitor) |
| Mifepristone (VGX410, RU486) | Viral Genomix | HIV infection (gene therapy,interferes with vpr) |
| MK-0518 | Merck | HIV infection (integase inhibitor) |
| PA-457 (bevirimat) | Panacos Pharmaceuticals, Inc. | Treatment of HIV (maturation inhibitor) |
| Poly(I)-Poly(C12U) (Ampligen) | Hemispherx Biopharma, Inc. | Biological response modifier |
| PPL-100 | Merck | HIV infection (protease inhibitor) |
| PRO 140 | Progenics Pharmaceuticals, Inc. | HIV infection (entry and fusion inhibitor) |
| PRO 542 | Progenics Pharmaceuticals, Inc. | HIV infection (entry and fusion inhibitor) |
| PRO 2000 | Indevus Pharmaceuticals, Inc. | Microbicide |
| Racivir | Pharmasset, Inc. | HIV infection (nucleoside RT inhibitor) |
| SCH-D (vicriviroc) | Schering-Plough Corp | HIV infection (entry and fusion inhibitor) |
| SP01A | Samaritan Pharmaceuticals | HIV infection (entry and fusion inhibitor) |
| SPL7013 | Starpharma | Microbicide |
| TAK-652 | Takeda | HIV infection (entry and fusion inhibitor) |
| Tipranavir (Aptivus) | Boehringer Ingelheim Pharmaceuticals | HIV infection (protease inhibitor) |
| TNX-355 | Tanox, Inc. | HIV infection (entry and fusion inhibitor) |
| TMC125 (etravirine) | Tibotec | HIV infection (non-nucleoside RT inhibitor) |
| UC-781 | Cellegy Pharmaceuticals, Inc | Microbicide |
| UK-427,857 (Maraviroc) | Pfizer | HIV infection (entry and fusion inhibitor) |
| Valproic acid | Abbott | Treating seizures in HIV infection |
| VRX496 | VIRxSYS | Gene therapy |
| Zalcitabine (Hivid) | Roche | HIV infection (nucleoside T inhibitor) |
| Valganciclovir (Valcyte) | Roche | Antiviral (CMV retinitis in AIDS) |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |

| Drug Name | Manufacturer Examples | Therapeutic Use |
| --- | --- | --- |
| Piritrexim | Burroughs Wellcome | PCP treatment |
| Pentamidine isethionate | Fisons Corporation | PCP prophylaxis |
| Spiramycin | Rhone-Poulenc | Cryptosporidial diarrhea |
| Intraconazole-R51211 | Janssen Pharm | Histoplasmosis; cryptococcal meningitis |
| Trimetrexate | Warner-Lambert | PCP |
| Daunorubicin | NeXstar, Sequus | Karposi's sarcoma |
| Recombinant Human Erythropoietin | Ortho Pharm. Corp. | Severe anemia assocated w/AZT therapy |
| Recombinant Human Growth Hormone | Serono | AIDS-related wasting, cachexia |
| Megestrol Acetate | Bristol-Myers Squibb | Treatment of anorexia associated w/AIDS |
| Testosterone | Alza, Smith Kline | AIDS-related wasting |
| Total Enteral Nutrition | Norwich Eaton Pharmaceuticals | Diarrhea and malabsorption in AIDS |
| Aldesleukin (Proleukin) | Chiron Corp | Biological response modifier |
| Amphotericin B (Abelecet, AmBisome, Amphocin, Amphotec, Fungizone) | Pfizer, Bristol-Myers Squibb | Antifungal |
| Azithromycin (Zithromax) | Pfizer | Antibacterial antibiotic |
| Calcium hydroxyapatite (Radiesse | Bioform Medical, Inc. | Dermal filler |
| Doxorubicin (liposomal) (Doxil) | Ortho Biotech, Alza Corporation | Antineoplastic |
| Dronabinol (Marinol) | Unimed Pharmaceuticals, Inc. | Antiemetics |
| Entecavir (Baraclude) | Bristol-Myers Squibb | Antiviral |
| Epoetin alfa (Epogen, Procrit) | Ortho Biotech | Anemia |
| Etoposide (Etopophos (phosphate salt), Toposar, VePesid) | Pfizer, Bristol-Myers Squibb | Antineoplastic |
| Fluconazole (Diflucan) | Pfizer | Antifungal |
| Interferon alfa-2 (Intron A (2b), Roferon-A (2a) | Roche, Schering-Plough | Biological response modifiers |
| Itraconazole (Sporanox) | Ortho Biotech, Janssen Pharmaceutica | Antifungal |
| Megestrol (Megace, Megace ES) | Bristol-Myers Squibb | Anticachectic |
| Paclitaxel (Onxol, Taxol) | Bristol-Myers Squibb, IVAX Pharmaceuticals | Antineoplastic |
| Peginterferon alfa-2 (PEG-Intron (2b), Pegasys (2a)) | Roche, Schering-Plough | Antiviral |
| Pentamidine (Nebupent) | American Pharmaceutical Partners, Fujisawa Health Care, Inc. | Antiprotozoal |
| Poly-L-lactic acid (Sculptra) | Dermik Laboratories | Dermal Filler |
| Somatropin | Pharmacia Corporation, Serono Inc | Synthetic human growth hormone |
| Sulfamethoxazole/ Trimethoprim (Bactrim, Septra) (Serostim) | Alpha care Inc, Women First Health Care, King Pharmaceuticals | Antibacterial |
| Testosterone (Androderm, Androgel, Depo-Testosterone) | Pfizer Inc, Unimed Pharmaceuticals, Inc., Alza Corporation, Watson Laboratories | Androgens |
| Trimetrexate (Neutrexin) | United States Bioscience Inc, Medimmune, Inc. | Antiprotozoal |

The combinations of the anti-TB compounds of this invention with AIDS antivirals (including anti-HIV integrase-based antivirals), other antivirals, another TB drug and/or a TB drug that is active against drug-resistant TB; immunomodulators, anti-infectives, antibiotics, vaccines, other therapeutic agents are not limited to the list in the above Table, but includes, in principle, any combination with any pharmaceutical composition useful for the treatment against infection by HIV or for treating AIDS or ARC. Preferred combinations are simultaneous or alternating treatments of a compound of the present invention and a protease inhibitor (e.g., indinavir, nelfinavir, ritonavir, saquinavir and others), a reverse transcriptase (RT) inhibitor (e.g., AZT, 3TC, ddC, ddI, d4T, abacavir and others), an integrase inhibitor (e.g., raltegravir, evitegravir) and/or non-nucleoside RT inhibitors (e.g., efavirenz, nevirapine, and others), or some combination of two or more of these inhibitors (see Table above). A few representative examples of relevant patents citing combinations are: EPO 0,484,071, U.S. Pat. No. 5,413,999, WO 9962513.

In such combinations, the compound of the present invention and other active agents may be separately administered or concurrently administered (coadministered). In addition, the administration of one element may be prior to, concurrent to, or subsequent to the administration of other agent(s).

Rifampin (Rifadin, Rimactane)
Rifapentine
Isoniazid (Nydrazid)
Ethambutol
Ethionamide
Para-aminosalicylic acid (PAS)
Capreomycin
Amikacin
Rifabutin (Mycobutin)
Streptomycin
Pyrazinamide
Cycloserine
Ciprofloxacin
Ofloxacin
Levofloxacin
Clofazimine
Bedaquiline
(−)βDioxolane-G; DXG;
(−)β-Arctigenin; Arctigenin;
(−)-Carbovir; (−)-C-D4G; (−)-Carbovir;
(+13-D-2,6-Diaminopurine dioxolane; Amdoxovir; DAPD; APD
(+)-2'-Deoxy-3'-oxa-4'-thiocytidine; dOTC (+)
(+)-2'-Deoxy-3'-oxa-4'-thio-5-fluorocytidine; dOTFC (+)
(+/−)-Cyclobut-G; A-69992; (+/−)-Lobucavir; C-Oxt-G; Cyclobut-G; C-Oxetanocin-G
(R)-2QuinCOAsnPhe[CHOHCH2]PipCONHtBu
(R)-3,6-Diamino-N-(aminomethyl)hexanamide; Bellenamine
(R)-PMPA; (R)-9-(2-Phosphonylmethoxypropyl)adenine; PMPA-(R); Tenofovir
(R)-PMPDAP; PMPDAP-(R)
(S)-PMPA; (S)-9-(2-Phosphonylmethoxypropyl)adenine; PMPA(S)
(S)-9-(2-Phosphonylmethoxypropyl)adenine; (S)-PMPA
α-APA; R89439; Loviride
α-APA deriv.; R87232
α-APA deriv.; R88703
α-APA enantiomer; R90385
α-L-AZT; AZT-α-L
α-L-DXC; α-L-Dioxalane-C; DXC-α-L-
α-L-FTC; FTC-α-L-
α-Monofluoromethyldehydroornithine methyl ester; MFMOME
1,1'-Azobisformamide; ADA; Azodicarbonamide
1-(11-Octylamino-10-hydroxyundecyl)-3,7-dimethylxanthine; CT-2576
1-(2',3'-Dideoxy-2'-fluoro-β-D-threo-pentofuranosyl)cytosine; Ro 31-6840
1-(2'-Fluoro-2',3'-dideoxy-B-D-erythro-pentofuranosyl)thymine; 2'FddT
1-(2OHPr)-4-Substit-piperazine, thienyl carbamate deriv.
1-(2OHPr)-4-Substit-piperazine, thienyl carbamate deriv.
1-(2OHPr)-4-Substit-piperazine, thienyl carbamate deriv.
1-(2OHPr)-4-Substit-piperazine, thienyl carbamate deriv.
1-[(2-Hydroxyethoxy)methyl]-6-(3-methylphenyl)thio)thymine; HEPT-M
1-[(2-Hydroxyethoxy)methyl]-6-(phenylthio)-2-thiothymine; HEPT-S
1-[(2-Hydroxyethoxy)methyl]-6-(phenylthio)thymine; HEPT
1-Deoxynojirimycin; Deoxynojirimycin
141 W94; VX-478; Amprenavir; Agenerase®; Approved
1592U89 Succinate; Abacavir Succinate; Ziagen® Approved
1-Aminooxyethylamine; AEA
1-Methoxyoxalyl-3,5-dicaffeoylquinic acid; 1-MO-3,5-DCQA; Dicaffeoylquinic acid deriv.
1OH-2(Cbz-Tle)3PhPr[14]paracyclophane deriv.
1OH-2(Cbz-ValNH)3PhPr[13]metacyclophane deriv.
1OH-2(Cbz-ValNH)3PhPr[13]paracyclophane deriv.
1OH-2(Cbz-ValNH)3PhPr[14]paracyclophane deriv.
1OH-2(Cbz-ValNH)3PhPr[17]paracyclophane deriv.
12-Deoxyphorbol-13-(3E,5E-decadienoate); Phorbol deriv.
16.alpha.-Bromoepiandrosterone; Epi-Br; Inactivin; HE 2000; HE2000; PPB2; DHEA deriv.
1-β-D-arabinofuranosyl-5-(2-bromovinyl)uracil; BV-ara-U; BVaraU; BV ara-U; Sorivudine; SQ-32756; Bravavir; Brovavir; Usevir; YN-72; Bromovinyl araU; BVAU
2',3'-Didehydro-3'-deoxycytidine; D4C
2',3'-Dideoxydidehydroguanosine; D4G
2',3'-Didehydro-3'-deoxythymidine; D4T; Stavudine; Zerit® Approved
2',3'-Dideoxy-3'-fluoro-4-thiothymidine; 3'-F-4-Thio-ddT
2',3'-Dideoxy-3'-fluoro-5-bromouridine; FddBrU
2',3'-Dideoxy-3'-fluoro-5-chlorocytidine; 3'-F-5-Cl-ddC
2',3'-Dideoxy-3'-fluoro-5-chlorouridine; 935U83; 5-Chloro-2',3'-dideoxy-3'-fluorouridine; FddClU; Raluridine
2',3'-Dideoxy-5-ethylcytidine; 5-Et-ddC
2',3'-Dideoxyadenosine; D2A; ddAdo; ddA
2',3'-Dideoxydidehydroadenosine; d4A
2',3'-Dideoxyguanosine; D2G; ddG
2',3'-Dideoxy-3'-hydroxymethyl cytidine; 3'-Hydroxymethyl-ddC; BEA-005
2,5'-Anhydro-3'-azido-2',3'-dideoxyuridine; AZU-2,5'-anhydro
2,5'-Anhydro-3'-azido-3'-deoxythymidine; AZT-2,5'-anhydro
2',5'diSilySpiroT; TSAO-T
2',5'diSilySpiroT; TSAO-me^3T
2,6-Diamino-2',3'-dideoxypurine-9-ribofuranoside; ddDAPR; DAPDDR; 2,6-Diamino-ddP
2,6-Diaminopurine-2',3'-dideoxydidehydroriboside; ddeDAPR
2,6-Diaminopurine-3'-fluoro-2',3'-dideoxyribo side; 3'-F-ddDAPR
2-Aminobenzylstatine Valyl Cbz deriv.; Statine deriv.
2-Glycine amide-5-chlorophenyl 2-pyrryl ketone; GCPK
[2-PyridCH2NCH3CO-Val-NHCH(Bz)]CHOHCHOH; A-77003
2'-Azido-2',3'-dideoxyadenosine; 9-(2'-Azido-2',3'-dideoxy-β-D-erythropentofuranosyl)adenine; 2'-N3ddA
2'-FddA(B-D-threo); F-ddA; 2'-F-dd-ara-A; 9-(2'-Fluoro-2',3'-dideoxy-B-D-threopentafuranosyl)adenine; Lodensine
2'-N3ddA (B-D-threo); 9-(2'-Azido-2',3'-dideoxy-β-threo-pentafuranosyl)adenine
2-NaphCOAsnPhe[CHOHCH2]Pro-OtBu
2-Nitrophenylphenylsulfone; NPPS
3-(3-Oxo-1-propenyl)-3'-azido-3'-deoxythymidine; 3-(3-Oxo-1-propenyl)AZT
3-(Phenylsulfonyl)-indole deriv.; L-737,126

3,5-DCQA; 3,5-Dicaffeoylquinic acid; Dicaffeoylquinic acid
3'-Azido-2',3'-dideoxy-5-[(cyanomethyl)oxy]uridine; 3'-N3-5-Cyanomethyloxy-ddU
3'-Azido-2',3'-dideoxy-5-aminouridine; 3'-N3-5-NH2-ddU
3'-Azido-2',3'-dideoxy-5-aza-6-deazauridine; C-analog of 3'-N3-ddU
3'-Azido-2',3'-dideoxy-5-bromouridine; 3'-N3-5-Br-ddU; AZddBrU
3'-Azido-2',3'-dideoxy-5-chlorocytidine; 3'-Az-5-Cl-ddC
3'-Azido-2',3'-dideoxy-5-dimethylaminouridine; 3'-N3-5-NMe2-ddU
3'-Azido-2',3'-dideoxy-5-ethyluridine; 3'-N3-5-EtddU; CS-85; AZddEtU
3'-Azido-2',3'-dideoxy-5-fluorocytidine; 3'-N3-5-F-ddC
3'-Azido-2',3'-dideoxy-5-fluorouridine; AZddFU
3'-Azido-2',3'-dideoxy-5-hydroxyuridine; 3'-N3-5-OH-ddU
3'-Azido-2',3'-dideoxy-5-iodouridine; 3'-N3-5-I-ddU; AZddIU
3'-Azido-2',3'-dideoxy-5-methyaminouridine; 3'-N3-5-NHMe-ddU
3'-Azido-2',3'-dideoxy-5-methylcytidine; CS-92; 3'-N3-5-Me-ddC
3'-Azido-2',3'-dideoxy-5-thiocyanatouridine; 3'-N3-5-SCN-ddU
3'-Azido-2',3'-dideoxy-5-trifluoromethyluridine; 3'-N3-5-CF3-ddU
3'-Azido-2',3'-dideoxycytidine; CS-91; 3'-N3-ddC
3'-Azido-2',3'-dideoxyguanosine; AZG; 3'-N3ddG
3'-Azido-2',3'-dideoxy-N4-5-dimethylcytidine; 3'-N3-N4-5-diMe-ddC
3'-Azido-2',3'-dideoxy-N4-OH-5-methylcytidine; 3'-N3-N4-OH-5-Me-ddC
3'-Azido-2',3'-dideoxyuridine; CS-87; 3'-N3ddU; AZdU; Uravidine
3'-Azido-3'-deoxy-6-azathymidine; 3'AZ-6AzaT
3-Azido-3'-deoxythymidilyl-(5',5')-2',3'-dideoxy-5'-adenylic acid; AZT-P-ddA
3'-Azido-3'-deoxythymidilyl-(5',5')-2',3'-dideoxy-5'-adenylic acid, 2-cyanoethyl ester; AZT-P(CyE)-ddA
3'-Azido-3'-deoxythymidilyl-(5',5')-2',3'-dideoxy-5'-inosinic acid; AZT-P-ddI
3'-Azido-3'-deoxythymidine-5'-(butylmethoxyvalinyl)phosphate; 5'MeOValPO3(Bu)AZT
3'-Azido-5-chloro-2',3'-dideoxyuridine; AzddClUrd; Azdd-ClU
3'-Deoxythymidine; ddT
3'-FddA (B-D-Erythro); 9-(3'-Fluoro-2',3'-dideoxy-B-D-erythropentafuranosyl)adenine
3'-FddC; 3'-Fluoro-2',3'-dideoxycytidine
3'-FddG; 3'-Fluoro-2',3'-dideoxyguanosine
3'-FddT; Alovudine; FddT; FddThD; 3'-FLT; FLT
3'-FddU; 3'-Fluoro-2',3'-dideoxyuridine
3'-Fluoro-2',3'-dideoxy-5-iodouridine; FddIU
3'-N3-ddA; 9-(3'-Azido-2',3'-dideoxy-B-D-erythropentafuranosyl)adenine
3TC; Lamivudine; Epivir® Approved;
Lamivudine & Zidovudine; Combivir® 3TC & AZT; Approved
4'-Acetoamidophenyl4-guadinobenzoate; AGB
4'-Az-3'-dT; 4'-Azido-3'-deoxythymidine
4'-Az-5CldU; 4'-Azido-5-chloro-2'-deoxyuridine
4'-AzdA; 4'-Azido-2'-deoxyadenosine
4'-AzdC; 4'-Azido-2'-deoxycytidine
4'-AzdG; 4'-Azido-2'-deoxyguanosine
4'-AzdI; 4'-Azido-2'-deoxyinosine
4'-AzdU; 4'-Azido-2'-deoxyuridine
4'-Azido-2'-deoxy-β-D-erythro-pentofuranosyl-5-methyl-2,4-dioxopyrimidine; 4'-Azidothymidine
4'-Cyanothymidine; 4'-CN-T
4-Methyl-5-(pyrazinyl)-3H-1,2-dithiole-3-thione; Oltipraz
5'-[(1,4-Dihydro-1-methyl-3-pyridinylcarbonyl)oxy]-3'-azido-2',3'-deoxythymidine; DP-AZT; HP-AZT; AZT Prodrug; AZT-DHP
5'-[[(Z)-4-amino-2-butenyl]methylamino]-5'-deoxyadenosine; MDL 73811
5'-Alkylglycosidecarbonate of 3'-azido-3'-deoxythymidine; AcNHGlc-hexyl-CO3 AZT
5Cl3PhS-2IndolCONH2
5-Fluoro-2',3'-dideoxycytidine; 5-F-ddC
5-Methyl-3'-azido-2',3'-dideoxyisocytidine; MeAZddIsoC
6-O-Butanoylcastanospermine; BuCast; MDL 28,574; Celgosivir
6-Chloro-9-(2,3-dideoxy-b-D-glyceropentofuranosyl)-9H-purine; D2ClP; 6-Chloro-ddP; CPDDR; 6Cl-ddP
6-Dimethylaminopurine-2',3'-dideoxyriboside; N-6-dimethyldddA; DMAPDDR
7-Chloro-N-methyl-5-(1H-pyrrol-2-yl)-3H-1,4-benzodiazepin-2-amine; Ro 24-7429
7-Chloro-5-(2-pyrryl)-3H-1,4-benzodiazepin-2(H)-one; Ro 5-3335
8-Chloro-TIBO; Tivirapine; R86183
9-(2,3-Dideoxy-β-D-ribofuranosyl)-6-(methylthio)purine; D2SMeP
9-[Bis(OHMe)cBu]A; A-69463; Cyclobutyl-A; Cyclobut-A; C-oxetanocin A
A-76890
A-77212
A-80987; Ritonavir deriv., A-81525; Ritonavir deriv., A-83962; Ritonavir deriv.
A-98881; Azacyclic urea deriv.
AA; L-ascorbic acid; Calcium Ascorbate
AAP-BHAP; U-104489; PNU-104489
Abacavir & Lamivudine & Zidovudine; Trizivir® ABC & (−)-3TC & AZT
ABT-378; Lopinavir; Component of Kaletra; Aluviran®
ABT-378 & ABT-538; Kaletra®; Lopinavir & Ritonavir; Aluviran® & Norvir®
ABT-538; Norvir®; Ritonavir; Component of Kaletra; Approved
Acemannan
Adefovir; PMEA; GS-0393
Adefovir dipivoxil; BisPom PMEA; GS-840; Preveon®
AG-1343; Viracept®; Nelfinavir; Approved
AG1350; LY316957; Nelfinavir-octahydro-thienopyridine analog
AHPBA analog; R-87366
Alpha-lipoic acid; α-Lipoic acid; Thioctic acid
ALX40-4C
AMD3100; JM3100
Amprenavir phosphate; VX-175; GW433908; GW433908A (*Sodium Salt*); GW433908G (*Calcium Salt*); Fosamprenavir
Ancer 20; Z-100
Anti-sense 25-mer phosphorothioate; GEM91
Atazanavir; CGP-73547; BMS-232632; BMS 232632; Zrivada; Latazanavir; Reyataz®
Atevirdine; U-87201E; BHAP deriv.
Aurintricarboxylic acid; Dupont ATA; Dupont DA639; SD-095345; ATA
AY 9944; trans-1,4-Bis(2-dichlorobenzylaminoethyl)cyclohexane dichlorhydrate
AZT; Zidovudine; Azidothymidine; Retrovir®

AZT-PO3(CH3)-AZT; O,O'-Bis(3'-azido-3'-deoxythymidin-5'-yl)methylphosphonate
Baicalin; TJN-151
Betulinic acid; Mairin
Betulinic acid, 3-O-(3',3'-dimethylsuccinate)
BHAP deriv.
BHAP deriv.; Rescriptor®; Delavirdine; U-90152
BHAP deriv.; U-88204E
BI-RG-587; Nevirapine; Viramune® Approved
BILA 1906 BS, BILA 2011 BS; Palinavir, BILA 2185 BS
Bis(2-nitrophenyl)sulfone; Bis(2NO2Ph)SO2; NSC633001
bis-ValHOEt-N2aza-peptide isostere; CGP 53820
bis-ValHOEt-N2aza-peptide isostere; CGP 53820 analog
BMS-186318
BocPhe[CHOH(CH2)3CH=CHPhCO]IleAMBI; L-687,908
BzOCValPhe[diCHOH(RR)]PheValBzOC
BzOCValPhe[diCHOH(SS)]PheValBzOC
C2-Sym Phosphinic amide deriv. (HOECHST AG)
Calanolide A; NSC675451, Calanolide B
Capravirine; S-1153
Castanospermine
CbzAF(CHOHCH2)AVVOMe
Cbz-Asn-Apns-Pro-NH-tBu; KNI-102
CGP 61755; Lasinavir, CGP 64222
CNI-H0294
Coactinon; I-EBU; HEPT deriv.; MKC-442; Emivirine
Conocurvone; NSC650891
Coviracil; (−)FTC; (−)-2',3'-Dideoxy-5-fluoro-3'-thiacytidine; Emtricitabine; Emtriva
C-Oxetanocin-G; A-69992; (+−)Lobucavir; C-Oxt-G; Cyclobut-G; (+−)Cyclobut-G
Crixivan®; Indinavir; MK639; L-735,524; Approved
Curdlan Sulfate
CV-N; Cyanovirin-N
Cyclic Urea Amide; SD 146
Cyclosporin A; Sandimmune®
[Me-Ile-4]Cyclosporin A; SDZ NIM 811
D4A (L); L-2',3'-Didehydro-2',3'-dideoxyadenosine
D4FC; D-D4FC; 2',3'-Didehydro-2',3'-dideoxy-5-fluorocytidine; DPC 817
D4FC (L); L-2',3'-Didehydro-2',3'-dideoxy-5-fluorocytidine
D4G (L); L-2',3'-Didehydro-2',3'-dideoxyguanosine
D4I (L); L-2',3'-Didehydro-2',3'-dideoxyinosine
DABO
ddC; Dideoxycytidine; Zalcitabine; Hivid®
ddI; Dideoxyinosine; Didanosine; Videx®
Dehydroepiandrosterone; DHEA; Prasterone; Dehydroisoandrosterone; EL-10
Dextran Sulfate
Dicaffeic acid ester; L-Chicoric acid
DMP-266; Sustiva®; Efavirenz; Approved
DMP-323; XM-323
DMP-450
Docosanol; n-Docosanol
dOTC (−); (−)-2'-Deoxy-3'-oxa-4'-thiocytidine
dOTFC (−); (−)-2'-Deoxy-3'-oxa-4'-thio-5-fluorocytidine
DP-178; Pentafuside; T-20; GP41 127-162 AA; Enfuvirtide; Fuzeon®
E-BPTU; HEPT deriv.; NSC 648400
E-EBU; HEPT deriv.; MKC-442 deriv.
E-EBU-dM; HEPT deriv.; MKC-442 deriv.
E-EPSeU; HEPT deriv.; MKC-442 deriv.
E-EPU; HEPT deriv.; MKC-442 deriv.
Ebselen
Etoposide
Epoxy steriod deriv.; (4α,5α,17β)-17-Hydroxy-3-oxo-4,5-epoxyandrostane-2-carboxamide
Eulicin
Fenalamide A1; Phenalamide A1; Stipiamide
Fleephilone
Fluoroquinolone deriv.; K-12
Fortovase®; Invirase®; Saquinavir; Ro31-8959; Approved
Foscarnet; Phosphonoformic acid; Foscavir;
FPMDAP, FPMPA, FPMPG
GPGRAF Octomer; SPC3
Hammerhead anti-gag RNA Ribozyme B
Harziphilone
HBY 097; Quinoxaline deriv.
HEPT deriv.; MKC-442 deriv.
HOCH2CH2 isostere; ThienopyridCON thienyl urethane deriv.
HOCH2CH2 isostere; ThienopyridCONthienyl urethane deriv.; LY326188
HPMPA
HPMPDAP
HU; Hydroxyurea; Hydrea
Hydroxocobalamin
Hypericin
Ingenol 3,5,20-triacetate; ITA; RD3-2118
Ingenol deriv.; RD4-2138
Inophyllum B, Inophyllum P
iQoa-Mta-Apns-Thz-NH-tBu; KNI-272
Isentress (Raltegravir)
IsoquinCON furanyl urethane analog
IsoquinCON thienyl urethane analog
KNI-154; Noa-Asn-Apns-Thz-NH-tBu, KNI-174; Noa-Asn-Apns-Dmt-NH-tBu
KNI-227; Qoa-Mta-Apns-Thz-NH-tBu
L-685,434, L-685,434-6-Hydroxy derivative, L-685,434-OEtMorphderivative; L-689,502
L-685,434-OEtNMe2, L-685,434-OPrMorph derivative, L-697,593; 2-Pyridinone deriv.
L-697,639; 2-Pyridinone deriv., L-697,661; 2-Pyridinone deriv.
L-FddC; β-L-5F-ddC
Lamivudine & Zidovudine; Combivir® 3TC & AZT; Approved
LY289612, LY289612 analog, LY289612 analog
LY-300046-HCl; PETT deriv.; Trovirdine
LY314163; Saquinavir/Nelfinavir deriv.
LY-73497; N-(2-Phenethyl)-N'-(2-thiazolyl)thiourea; PETT
MAP; Methyl acetylenic putrescine
Michellamine A; NSC650898, Michellamine B; NSC649324, Michellamine F
N-6-Et-ddA; N-Ethyl-2',3'-dideoxyadenosine
N-6-methyl ddA; N6-Methyl-2',3'-dideoxyadenosine
Naphthalene 2-sulphonate polymer; PRO 2000
Nelfinavir-octahydro-thienopyridine analog
Nonoxynol 9
NSC625487; Thiazolobenzimidazole; TBZ
Oxathiin deriv.; UC-38, Oxathiin deriv.; UC-84
P9941
Penicillin Et(NH)2 Sym dimer, Penicillin G, ET(NH)2 deriv.
Penicillin, 2Isoquin-OHPrNH2 analog
Pentosan Sulfate; Elmiron; SP54; Xylan Sulfate;
PETT Cl, F deriv., PETT deriv.
Phenoxan
Phorbol deriv.; Prostratin
Platanic acid
PMEDAP, PMEG, PMEHx; PMEI, PMEMAP, PMET
PNU-140690; U-140690; Tipranavir
Pyridinone deriv.
Quinoxalin2thione deriv; S-2720
R14458; TIBO deriv.
R82150; TIBO deriv.
R82913; TIBO deriv.
Resobene
Ribavirin; Virazole
Ro 31-8959-bis-thf deriv.

Saquinavir/Nelfinavir deriv.
SB-205569; Val-Phe-Phe-HOCH2CH2 isostere analog
SC-52151; Telinavir
SDZ PRI 053
Suramin Sodium
T22
Thalidomide
Thiangazole; (−)-Thiangazole, Thiazoloisoindol-5-one, Thiazoloisoindol-5-one, deriv.
Tle-Val-Sta, 5PhBuCOOH deriv.; Statine deriv.
UC-781
Val-Val-Sta, 5PhBuCOOH deriv.; Statine deriv.
VB-11,328
Viread®; Tenofovir Disoproxil An alternative list of drugs and/or bioactive agents useful in the treatment of TB infections, or conditions or disease states which are secondary to TB infections is set forth herein below. One or more of these agents may be used in combination (coadministered) with at least one anti-MDR TB agent as otherwise disclosed herein to treat MDR-TB or other drug-resistant TB and co-infections with other conditions or disease states, including AIDS/ARC, Kaposi's sarcoma, hepatitis B and C virus infections, and other microbial infections. When used, these compounds are also included in effective amounts.

These list of drugs and/or bioactive agents include those at the following website: aidsinfo.nih.gov/DrugsNew/DrugDetailNT.aspx?MenuItem=Drugs&Search=On&int_id=257 FDA Approved: *Tuberculosis* Rifampin (Rifadin, Rimactane); Rifapentine; Isoniazid (Nydrazid); Ethambutol; Ethambutol Hydrochloride; Ethionamide; Para-aminosalicylic acid (PAS); Capreomycin; Amikacin; Rifabutin (Mycobutin); Streptomycin; Pyrazinamide; Cycloserine; Ciprofloxacin; Ofloxacin; Levofloxacin; Clofazimine; Bedaquiline; Moxifloxacin Hydrochloride; HIV Combination Drugs Atripla; Combivir; Complera; Epzicom; Kaletra; Stribild; Trizivir; Truvada; Entry and Fusion Inhibitors Enfuvirtide; Maraviroc; Integrase Inhibitors Raltegravir; Non-nucleoside Reverse Transcriptase Inhibitors Delavirdine; Efavirenz; Etravirine; Nevirapine; Rilpivirine Nucleoside Reverse Transcriptase Inhibitors Abacavir; Abacavir/Lamivudine; Abacavir/Lamivudine/Zidovudine; Didanosine; Emtricitabine; Emtricitabine/Tenofovir Disoproxil Fumarate; Lamivudine; Lamivudine/Zidovudine; Stavudine; Tenofovir Disoproxil Fumarate; Zidovudine Protease Inhibitors Atazanavir; Darunavir; Fosamprenavir; Indinavir; Lopinavir/Ritonavir; Nelfinavir; Ritonavir; Saquinavir; Tipranavir. Opportunistic Infections Aspergillosis; Amphotericin B; Voriconazole; Coccidioidomycosis; Amphotericin B; Fluconazole; Itraconazole; Cryptococcosis; Amphotericin B; Fluconazole; Flucytosine; Itraconazole; Cryptosporidiosis/Microsporidiosis Albendazole; Itraconazole; Cytomegalovirus Disease Foscarnet Sodium; GanciClovir; Valganciclovir Hydrochloride; Disseminated *Mycobacterium avium* Complex Disease Azithromycin; Ciprofloxacin; Clarithromycin; Ethambutol Hydrochloride; Levofloxacin; Moxifloxacin Hydrochloride; Rifabutin; Hepatitis B Virus Infection Hepatitis B Vaccine; Peginterferon Alfa-2a; Hepatitis C Virus Infection Peginterferon Alfa-2a; Peginterferon Alfa-2b; Ribavirin; Herpes Simplex Virus Disease Acyclovir; Famciclovir; Foscarnet Sodium; Imiquimod; Valacyclovir Hydrochloride; Histoplasmosis Amphotericin B; Itraconazole; Human Herpesvirus-8 Diseases Ganciclovir; Valganciclovir Hydrochloride; Isosporiasis Ciprofloxacin; Pyrimethamine; Sulfamethoxazole/Trimethoprim; Leishmaniasis Amphotericin B; Mucocutaneous Candidiasis Amphotericin B; Butoconazole Nitrate; Clotrimazole; Fluconazole; Itraconazole; Miconazole; Terconazole; Voriconazole; *Penicilliosis marneffei* Amphotericin B; Itraconazole; *Pneumocystis*; Pneumonia Clindamycin; Primaquine Phosphate; PyrimethamineiSulfamethoxazole/Trimethoprim; *Toxoplasma gondii* Encephalitis Azithromycin; Clindamycin; Pyrimethamine; Sulfadiazine; Sulfamethoxazole/Trimethoprim; Varicella-Zoster Virus Diseases Acyclovir; Famciclovir; Foscarnet Sodium; Ganciclovir; Valacyclovir Hydrochloride; Varicella Virus Vaccine Live Investigational: HIV Entry and Fusion Inhibitors AMD-070; BMS-663068; Cenicriviroc; INCB-9471; Ibalizumab; PRO-140: Integrase Inhibitors Dolutegravir; S/GSK1265744; Non-nucleoside Reverse Transcriptase Inhibitors Lersivirine; Nucleoside Reverse Transcriptase Inhibitors BMS-986001; Elvucitabine; GS-7340; Racivir.

Chemical Synthesis: General Synthetic Scheme

A general scheme for the synthesis is shown below in Scheme 1. The precursors to the target molecules are indicated. These precursors were synthesized by modifications of methodologies developed in the Nair laboratory [J. Org. Chem. 72, 8577-8579 (2007); ACS Med. Chem. Lett. 2, 877-881 (2011); J. Med. Chem. 49, 445447 (2006); J. Am. Chem. Soc. 109, 7223-7224 (1987); J. Org. Chem. 53, 30513057 (1988)]. The key and most important step in the synthesis is the conversion of these precursors to the target molecules and the methodologies for these conversions are indicated.

Scheme 1

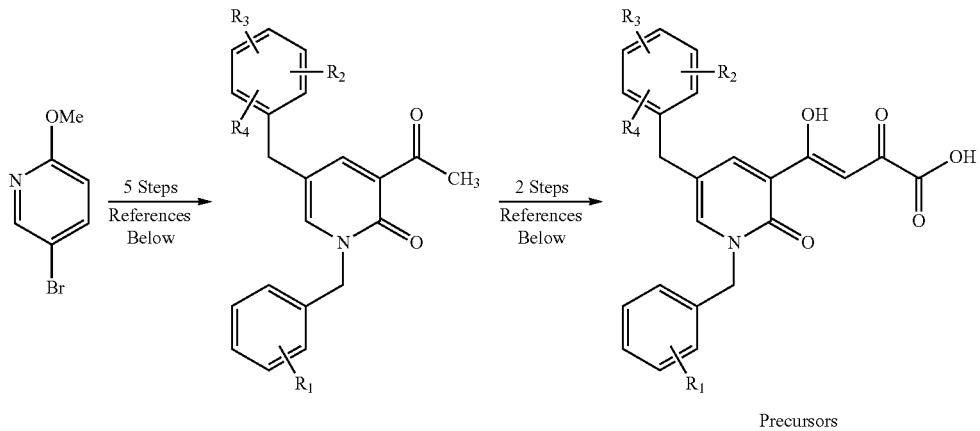

Precursors

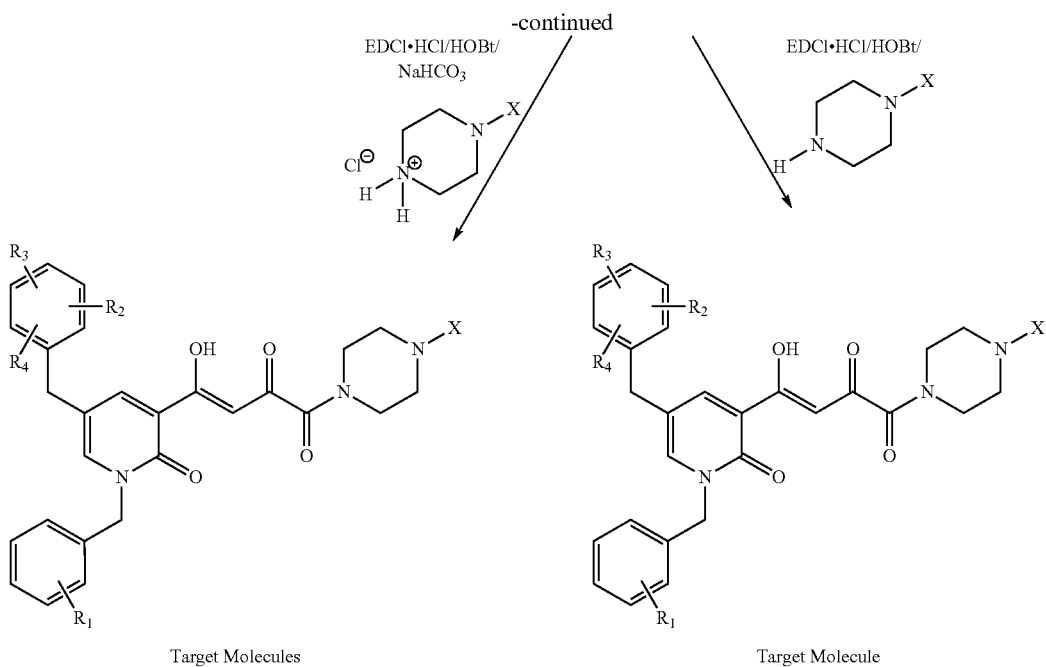

Target Molecules

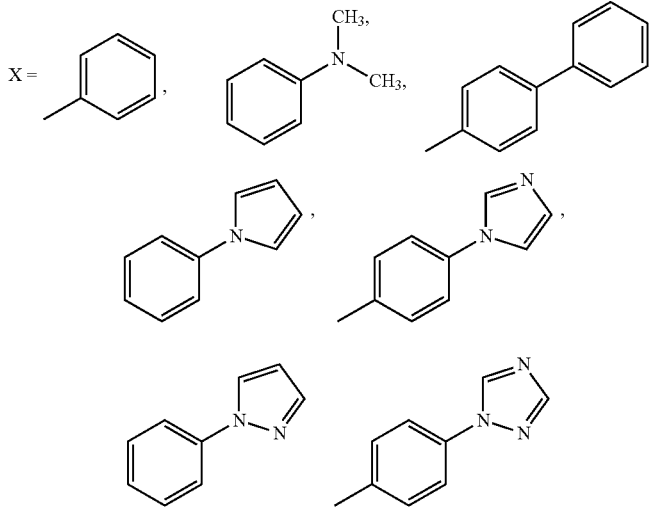

Target Molecule

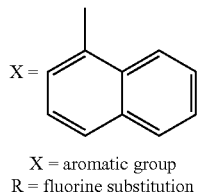

X = aromatic group
R = fluorine substitution

X = aromatic group or substituted aromatic group
R = fluorine substitution

Nair Laboratory References for Precursor Synthesis

1. J. Org. Chem. 72, 8577-8579 (2007).
2. ACS Med. Chem Lett., 2, 877-881 (2011).
3. J. Med. Chem. 49, 445-447 (2006).
4. J. Am. Chem. Soc. 1987, 109, 7223-7224 (1987).
5. J. Org. Chem. 53, 3051-3057 (1988).

CHEMICAL SYNTHESIS: REPRESENTATIVE EXAMPLES

The following representative examples are provided to illustrate details for the preparation of the compounds of the present invention. The examples are not intended to be limitations on the scope of the present invention and they should not be so construed. Furthermore, the compounds described in the following examples are not to be viewed as forming the only set of compounds that is considered as the invention, and any combination of components of the compounds or their moieties may itself form a set. This has been addressed previously in this patent document. Those skilled in the art will readily comprehend that known variations of reaction conditions and synthetic conversions described in the following preparative procedures can be used to readily prepare these other compounds routinely.

Representative Example 1

4-(1-(2-Fluorobenzyl)-2-oxo-5-(2,4,6-trifluorobenzyl)-1,2-dihydropyridin-3-yl)-4-hydroxy-1-(4-(naphthalen-1-yl)piperazin-1-yl)but-3-ene-1,2-dione (2)

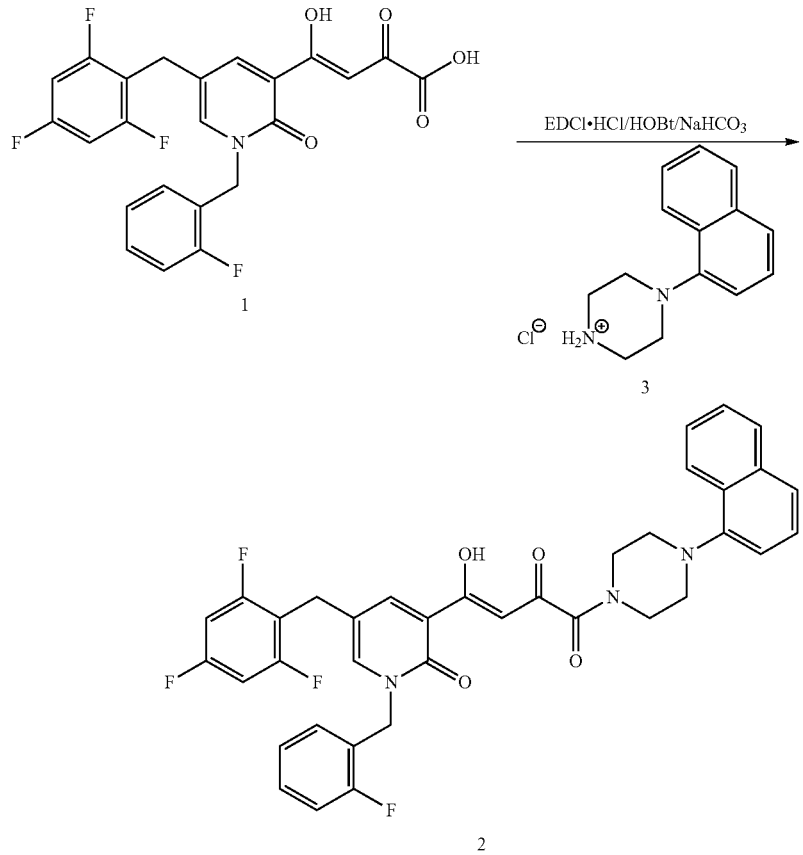

To a chilled solution of 4-(1-(2-fluorobenzyl)-2-oxo-5-(2,4,6-trifluorobenzyl)-1,2-dihydropyridin-3-yl)-4-hydroxy-2-oxobut-3-enoic acid 1, prepared using modifications of methodologies previously described by us, *J. Org. Chem.* 72, 8577-8579 (2007); ACS Med. Chem. Lett. 2, 877-881 (2011), (103 mg, 0.224 mmol) in dimethylformamide (DMF) (1.3 mL) was added hydroxybenzotriazole (HOBT) (33 mg, 0.246 mmol), followed by 1-(3-dimethylaminopropyl)-3-ethylcarbodiimide hydrochloride (EDCI-HCl) (47 mg, 0.246 mmol). The mixture was stirred at 0° C. for 20 minutes and then 4-(naphthalen-1-yl)piperazin-1-ium chloride 3, (61 mg, 0.2463 mmol) and NaHCO$_3$ (21 mg, 0.246 mmol) were added. Stirring was continued for 2.5 h at 0° C. Water was then added to precipitate the product, which was filtered and washed with additional water. This solid was dissolved in ethyl acetate (50 mL) and the solution washed with water (4×50 mL) The ethyl acetate extract was concentrated in vacuo and the resulting oily product was dried in vacuo to give the crude product, which was passed through a short silica gel column with chloroform as the eluting solvent. The eluent was removed and the residue was triturated with pentane to give a yellow amorphous powder (44.1 mg, 30%). UV (methanol): λ 387 nm (ε 16,349); 305 nm (ε 10,899). $^1$H-NMR (DMSO-d$_6$, 500 MHz), δ 15.00 (bs, 1H), 8.21-8.12 (m, 3H), 7.95-7.91 (m, 1H), 7.68-7.00 (m, 12H), 5.25 (bs, 214), 3.88-3.74 (m, 6H), 3.74-2.82 (m, 4H). HRMS: calculated mass 656.2172 for C$_{37}$H$_{30}$F$_4$N$_3$O$_4$[M+H]$^+$; found 656.2170.

Representative Example 2

4-(1,5-Dibenzyl-2-oxo-1,2-dihydropyridin-3-yl)-4-hydroxy-1-(4-(naphthalen-1-yl)piperazin-1-yl)but-3-ene-1,2-dione (4)

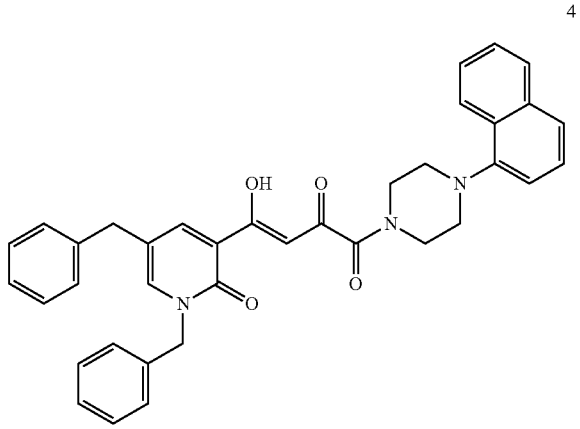 [SMILES: O=C(/C=C(\O)c1cc(Cc2ccccc2)cn(Cc2ccccc2)c1=O)C(=O)N1CCN(c2cccc3ccccc23)CC1]

The title compound 4 was synthesized using the procedure described above for compound 2 using 4-(1,5-dibenzyl- 2-oxo-1,2-dihydropyridin-3-yl)-4-hydroxy-2-oxobut-3-enoic acid as the precursor. The product was isolated as a yellow solid. UV (methanol): λ 390 nm (ε 15,333), 302 nm (ε 10,810). $^1$H-NMR (DMSO-$d_6$, 500 MHz), δ 15.04 (bs, 1H), 8.34 (bs, 8.19 (m, 114), 7.91 (m, 1H), 7.65 (m, 1H), 7.55-7.16 (m, 16H), 5.23 (s, 2H), 3.86-3.73 (m, 6H), 3.04 (m, 4H).

HRMS: calculated mass 584.2549 for $C_{37}H_{34}N_3O_4$ [M+H]$^+$; found 584.2543.

Representative Example 3

1-(4-([1,1'-Biphenyl]-4-yl)piperazin-1-yl)-4-(1-(2-fluorobenzyl)-2-oxo-5-(2,4,6-trifluorobenzyl)-1,2-dihydropyridin-3-yl)-4-hydroxybut-3-ene-1,2-dione (5)

ethylcarbodiimide hydrochloride (EDCI-HCl) (46 mg, 0.238 mmol). The mixture was stirred for 30 minutes, treated with 1-([1,1'-biphenyl]-4-yl)piperazine 6, (57 mg, 0.238 mmol) and the resulting reaction mixture was stirred for 2.5 h at 0° C. Water was then added to precipitate the product, which was filtered and washed with additional water. This solid was dissolved in ethyl acetate (50 mL) and the solution washed with water (4×50 mL) and finally with brine (100 mL). The ethyl acetate extract was concentrated in vacuo and the resulting oily product was dried in vacuo to give the crude product, which was passed through a short silica gel column with chloroform as the eluting solvent. The eluent was removed and the residue was triturated with pentane to give a yellow amorphous powder (83 mg, 56%). UV (methanol): λ 389 nm (ε 16,746), λ 284 nm (ε 27,712). $^1$H-NMR

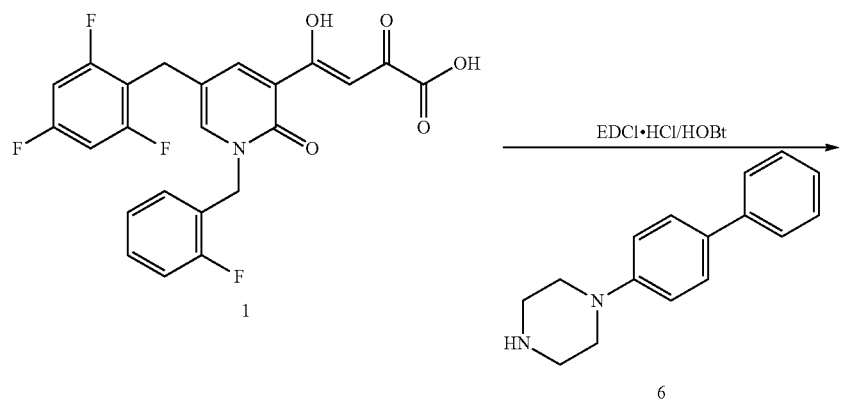

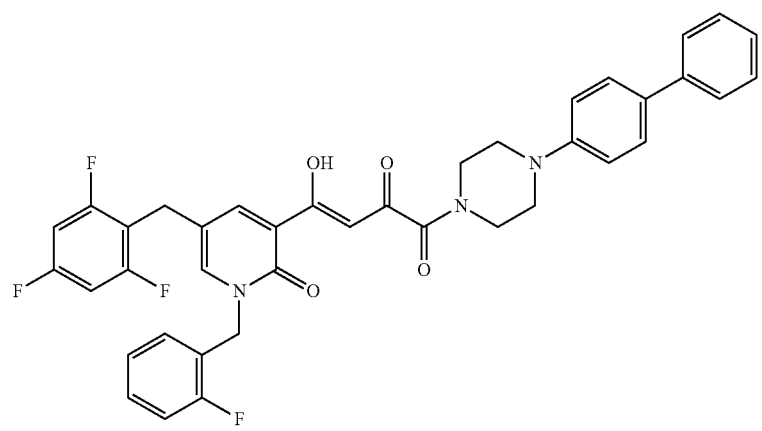

To a chilled solution of 4-(1-(2-fluorobenzyl)-2-oxo-5-(2,4,6-trifluorobenzyl)-1,2-dihydropyridin-3-yl)-4-hydroxy-2-oxobut-3-enoic acid 1, (100 mg, 0.217 mmol) in DMF (1.3 mL) was added hydroxybenzotriazole (HOBT) (32 mg, 0.238 mmol), followed by 1-(3-dimethylaminopropyl)-3-

(CDCl$_3$, 500 MHz), δ 15.15 (bs, 1H), 8.24 (m, 1H), 7.60-7.03 (m, 19H), 6.74 (t, 2H), 5.20 (bs, 2H), 3.88-3.86 (m, 2H), 3.80 (s, 2H), 3.78-3.75 (m, 2H), 3.34-3.21 (m, 4H). HRMS: calculated mass 682.2329 for $C_{39}H_{32}F_4N_3O_4$ [M+H]$^+$; found 682.2326.

Representative Example 4

1-(4-(4-(1H-imidazol-1-yl)phenyl)piperazin-1-yl)-4-(1-(2-fluorobenzyl)-2-oxo-5-(2,4,6-trifluorobenzyl)-1,2-dihydropyridin-3-yl)-4-hydroxybut-2-ene-1,4-dione (7)

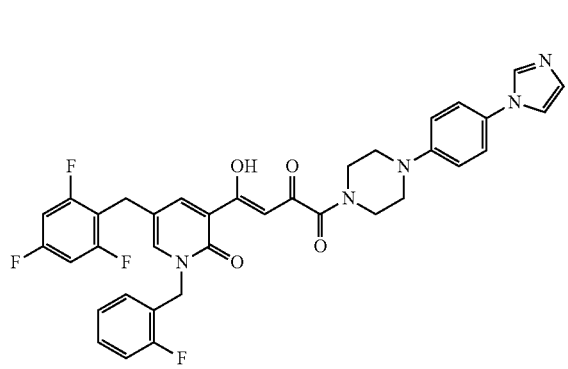

The title compound 7 was synthesized by the procedure described above for compound 5 using appropriate precursors. The product was a yellow solid. UV (methanol): λ 389 nm (ε 15,521), 266 nm (ε 23,131). $^1$H-NMR (CDCl$_3$, 500 MHz): δ 8.19-8.20 (m, 1H), 7.79 (s, 1H), 7.50-7.57 (m, 2H), 7.42-7.45 (m, 1H), 7.28-7.33 (m, 3H), 7.19-7.23 (m, 2H), 7.06-7.14 (m, 2H), 6.94-6.99 (m, 2H), 6.69 (t, 2H, J=8.0 Hz), 5.16 (s, 2H), 3.71-3.83 (m, 6H), 3.16-3.28 (m, 4H), 1.25 (s, 1H). HRMS: calculated for $C_{36}H_{30}F_4N_5O_4$ [M+H]$^+$ 672.2234, found 672.2241.

Representative Example 5

1-(4-([1,1'-Biphenyl]-3-yl)piperazin-1-yl)-4-(1-(2-fluorobenzyl)-2-oxo-5-(2,4,6-trifluorobenzyl) 1,2-dihydropyridin-3-yl)-4-hydroxybut-3-ene-1,2-dione (8)

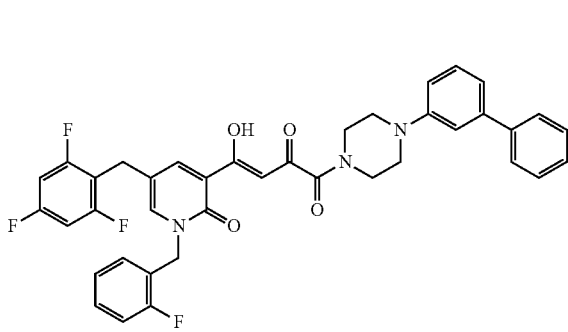

The title compound was synthesized by the procedure described above for compound 5 using appropriate precursors. The product was a yellow powder. UV (methanol): λ 388 nm (ε 13,958), 307 nm (ε 5,696), 241 nm (ε 35,609). $^1$H-NMR (CDCl$_3$, 500 MHz), δ 8.14 (bs, 1H), 7.51-7.19 (m, 10H), 7.08-7.00 (m, 4H), 6.86 (d, 1H), 6.65-6.61 (m, 2H), 5.08 (bs, 2-1), 3.77-3.67 (m, 6H), 3.23-3.12 (m, 4H). HRMS: calculated mass 682.2329 for $C_{39}H_{32}F_4N_3O_4$ [M+H]$^+$; found 682.2326.

Representative Example 6

1-(4-(4-(Dimethylamino)phenyl)piperazin-1-yl)-4-(1-(2-fluorobenzyl)-2-oxo-5-(2,4,6-trifluorobenzyl)-1,2-dihydropyridin-3-yl)-4-hydroxybut-3-ene-1,2-dione (9)

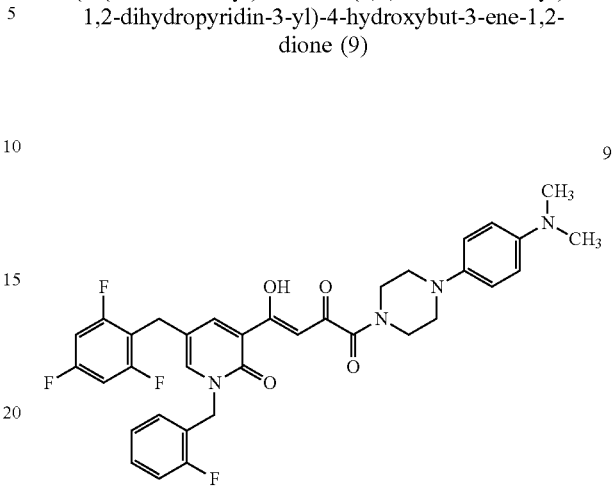

The title compound 9 was synthesized by the procedure described above for compound 5 using appropriate precursors. The product was a dark yellow solid. UV (methanol): λ 387 nm (ε 12,272), 315 nm (ε 5,766), 261 nm (ε 17,968). $^1$H-NMR (DMSO, 500 MHz): δ 8.20 (s, 1H), 8.14-8.05 (m, 1H), 7.38-7.18 (m, 7H), 6.88-6.69 (m, 4H), 5.25 (s, 2H), 3.88 (s, 2H), 3.67-3.47 (m, 4H), 3.35 (bs, 2H), 3.01-2.95 (m, 3H), 2.82-2.78 (m, 6H). HRMS: calculated mass 649.2438 for $C_{35}H_{33}F_4N_4O_4$ [M+H]$^+$; found 649.2414.

Representative Example 7

1-(4-(4-(1H-imidazol-1-yl)phenyl)piperazin-1-yl)-4-(1,5-dibenzyl-2-oxo-1,2-dihydropyridin-3-yl)-4-hydroxybut-3-ene-1,2-dione (10)

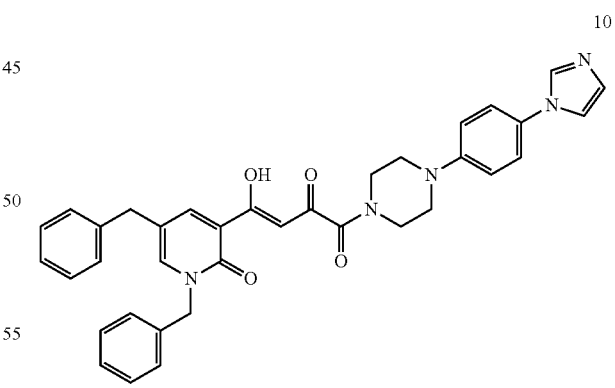

The title compound 10 was synthesized by the procedure described above for compound 5 using appropriate precursors. The product was a yellow solid. UV (methanol): λ 390 nm (ε 18,858), 266 nm (ε 29,129). $^1$H-NMR (CDCl$_3$, 500 MHz): δ 8.11, 8.13 (dd, 1H, J=2.5 Hz), 7.70 (s, 1H), 7.48 (s, 1H), 7.04-7.29 (m, 14H), 6.91 (d, 2H, J=8.5 Hz), 6.82 (d, 11-1, J=8.5 Hz), 5.07 (s, 2H), 3.59-3.76 (m, 6H), 2.95-3.20 (m, 4H). HRMS: Calculated for $C_{36}H_{34}N_5O_4$ [M+H]$^+$ 600.2611, found 600.2612.

Representative Example 8

1-(4-(4-(1H-pyrrol-1-yl)phenyl)piperazin-1-yl)-4-(1-(2-fluorobenzyl)-2-oxo-5-(2,4,6-trifluorobenzyl)-1,2-dihydropyridin-3-yl)-4-hydroxybut-3-ene-1,2-dione (11)

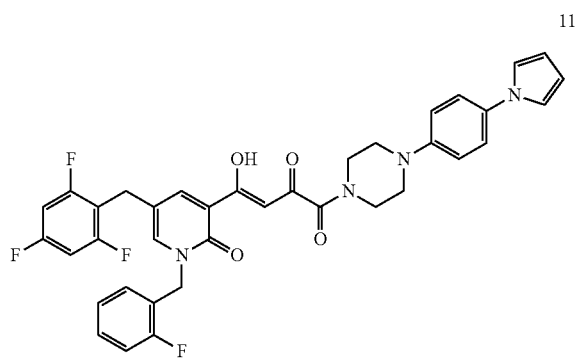 [SMILES: O=C(/C=C(\O)c1cc(Cc2c(F)cc(F)cc2F)cn(Cc2ccccc2F)c1=O)C(=O)N1CCN(c2ccc(-n3cccc3)cc2)CC1]

The title compound 11 was synthesized by the procedure described above for compound 5 using appropriate precursors. The product was a yellow solid. UV (methanol): λ 373 nm (ε 12,483), 269 nm (ε 28,993). $^1$H-NMR (CDCl$_3$, 500 MHz): δ 8.18, 8.20 (dd, 1H, J=3.0, 2.5 Hz), 7.50-7.55 (m, 2H), 7.44 (t, 1H, J=7.75 Hz), 7.29-7.33 (m, 4H), 6.92-7.14 (m, 6H), 6.66-6.71 (m, 2H), 6.31 (s, 2H), 5.16 (s, 2H), 3.70-3.83 (m, 6H), 3.12-3.24 (m, 4H). HRMS: calculated mass for C$_{37}$H$_{31}$F$_4$N$_4$O$_4$ [M+H]$^+$ 671.2281; found 671.2259.

Representative Example 9

1-(4-(4-(1H-pyrrol-1-yl)phenyl)piperazin-1-yl)-4-(1,5-dibenzyl-2-oxo-1,2-dihydropyridin-3-yl)-4-hydroxybut-3-ene-1,2-dione (12)

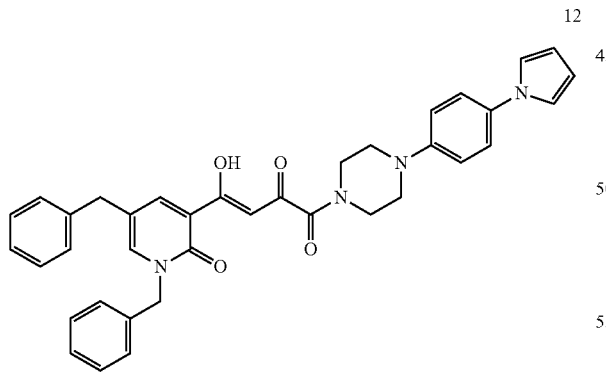

The title compound 12 was synthesized by the procedure described above for compound 5 using appropriate precursors. The product was a yellow solid. UV (methanol): λ 368 nm (ε 13,413), 271 nm (ε 29,880). $^1$H-NMR (CDCl$_3$, 500 MHz): δ 8.18, 8.21 (dd, 1H, J=3.0 Hz), 7.55 (s, 1H), 7.24-7.36 (m, 13H), 7.11-7.14 (m, 2H), 6.96-7.01 (m, 2H), 6.88 (d, 1H, J=8.0 Hz), 6.31 (t, 2H, J=2.0 Hz), 5.14 (s, 2H), 3.68-3.83 (m, 6H), 3.19-3.24 (m, 4H). HRMS: calculated mass 599.2658 for C$_{37}$H$_{35}$N$_4$O$_4$ [M+H]$^+$; found 599.2640.

Representative Example 10

1-(4-(4-(1H-pyrrol-1-yl)phenyl)piperazin-1-yl)-4-(5-(3,5-difluorobenzyl)-1-(2-fluorobenzyl)-2-oxo-1,2-dihydropyridin-3-yl)-4-hydroxybut-3-ene-1,2-dione (13)

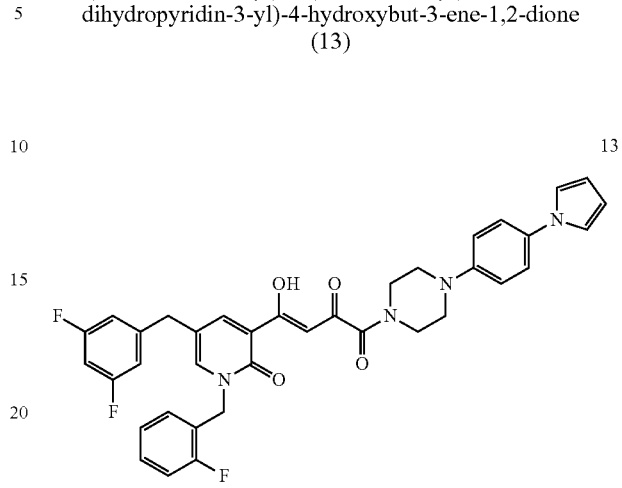

The title compound 13 was synthesized by the procedure described above for compound 5 using appropriate precursors. The product was a yellow solid. UV (methanol): 376 nm (ε 15,065), 269 nm (ε 31,601). $^1$H-NMR (CDCl$_3$, 500 MHz): δ 8.15 (d, 1H, J=2.5 Hz), 7.58 (s, 1H), 7.50-7.55 (m, 2H), 7.32-7.36 (m, 3H), 7.10-7.20 (m, 2H), 7.00-7.05 (m, 4H), 6.68-6.78 (m, 3H), 6.36 (t, 2H, J=1.75 Hz), 5.22 (s, 2H), 3.88 (bs, 2H), 3.80 (s, 2H), 3.77 (bs, 2H), 3.25-3.29 (m, 4H). HRMS: calculated mass 653.2376 for C$_{37}$H$_{32}$F$_3$N$_4$O$_4$ [M+H]$^+$; found 653.2357.

Representative Example 11

1-(4-(4-(1H-pyrrol-1-yl)phenyl)piperazin-1-yl)-4-(5-(2,6-difluorobenzyl)-1-(2-fluorobenzyl)-2-oxo-1,2-dihydropyridin-3-yl)-4-hydroxybut-3-ene-1,2-dione (14)

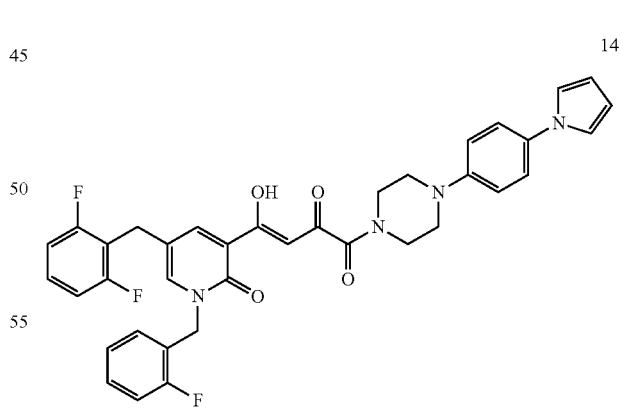

The title compound 14 was synthesized by the procedure described above for compound 5 using appropriate precursors. The product was a yellow solid. UV (methanol): λ 388 nm (ε 15,140), 269 nm (ε 25,878). $^1$H-NMR (CDCl$_3$, 500 MHz) δ 8.24 (s, 1H), 7.52-7.15 (m, 7H), 7.13-6.89 (m, 8H), 6.32 (s, 2H), 5.16-5.15 (m, 2H), 4.44 (s, 0.3H), 3.81-3.72 (m, 6H), 3.23-3.20 (m, 4H). HRMS: calculated mass 653.2376 for C$_{37}$H$_{32}$F$_3$N$_4$O$_4$ [M+H]$^+$; found 653.2360.

Representative Example 12

1-(4-(4-(1H-pyrrol-1-yl)phenyl)piperazin-1-yl)-4-(1-(2-fluorobenzyl)-5-(4-fluorobenzyl)-2-oxo-1,2-dihydropyridin-3-yl)-4-hydroxybut-3-ene-1,2-dione (15)

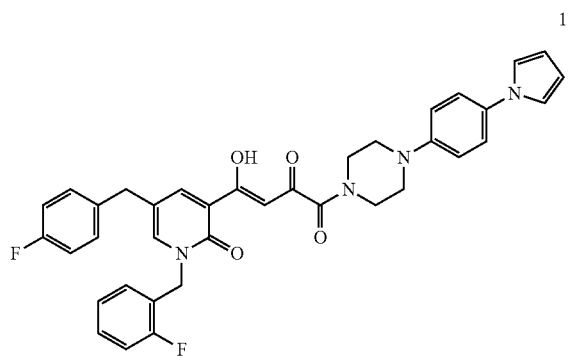

The title compound 15 was synthesized by the procedure described above for compound 5 using appropriate precursors. The product was a yellow solid. UV (methanol): λ 390 nm (ε 14,942), 269 nm (ε 25,779). $^1$H-NMR (CDCl$_3$, 500 MHz): δ 3.12-3.25 (m, 4H), 3.71-3.91 (m, 7H), 4.47 (s, 0.3H), 5.14-5.16 (m, 2H), 6.32-6.33 (m, 2H), 6.93-7.15 (m, 10H), 7.15-7.52 (m, 7H), 8.13-8.14 (m, 1H). HRMS: calculated mass 635.2470 for C$_{37}$H$_{33}$F$_2$N$_4$O$_4$ [M+H]$^+$; found 653.2451.

Representative Example 13

4-(1-(2-Fluorobenzyl)-2-oxo-5-(2,4,6-trifluorobenzyl)-1,2-dihydropyridin-3-yl)-4-hydroxy-1-(4-(naphthalen-1-yl)piperazin-1-yl)but-3-ene-1,2-dione (16)

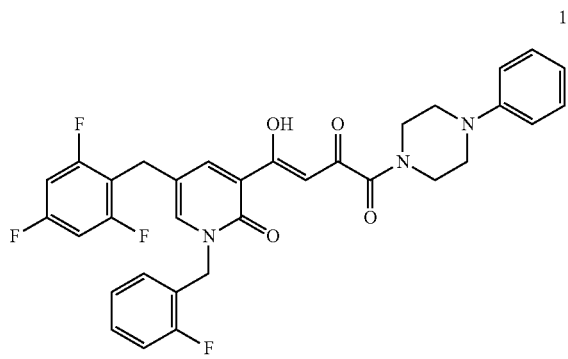

The title compound 16 was synthesized by the procedure described above for compound 2 using appropriate precursors. The product was a yellow solid. UV (methanol): λ 385 nm (ε 12,721), 247 nm (ε 11,768). $^1$H-NMR (CDCl$_3$, 500 MHz): δ=15.10-15.12 (m, 0.5H), 8.18-8.20 (m, 1H), 7.44-7.57 (m, 2H), 7.24-7.33 (m, 4H), 7.06-7.14 (m, 2H), 6.90-6.94 (m, 3H), 6.66-6.71 (m, 2H), 5.14-5.15 (m, 2H), 3.69-3.82 (m, 6H), 3.12-3.24 (m, 4H). HRMS: calculated mass 606.2016 for C$_{33}$H$_{28}$F$_4$N$_3$O$_4$ [M+H]$^+$; found 606.2012.

Biology
Method for Agar Dilution Drug Susceptibility Assays Against Multidrug-Resistant *Mycobacterium Tuberculosis* (MDR-TB)

The following assays were conducted against MDR-TB following the screening guidelines of the Clinical and Laboratory Standards Institute (CLSI).

Materials.

The compounds were stable at room temperature and were stored at room temperature until the day of the drug susceptibility assay. Prior to screening, the compounds were solubilized in a minimum amount of DMSO. The screening was done with an isolate of MDR-TB that was resistant to both isoniazid (INH) and rifampin (R). This isolate used for the screening assays was an aliquot from a working stock culture collection that had been stored frozen at −80° C. The aliquot was allowed to thaw at room temperature and subsequently diluted in test media. The screening assays used the following positive and negative controls: (a) organism only (negative control); (b) streptomycin (anti-MDR-TB drug, positive control).

Methods.

The agar dilution susceptibility assay method and format were utilized for susceptibility testing. The agar medium, Middlebrook 7H10 (BD BioSciences; Sparks, Md.), was prepared according to the manufacturer's guidelines and the test compounds were serially diluted two-fold to achieve a testing concentration range from 25 micrograms/mL to 0.012 micrograms/mL (total of 12 concentrations). Each concentration of compound was mixed with Middlebrook 7H10 agar, poured into sterile petri dishes (plates) and allowed to solidify. The plates were subsequently inoculated with approximately 2.0×10$^3$ CFU *M. tuberculosis* and incubated for 21 days at 37° C. Testing was conducted in triplicate and the MICs (minimum inhibitory concentrations) were reported as the lowest concentration (micrograms/mL) of drug that completely inhibited growth of the organism as visibly determined.

Activity.

Anti-MDR TB activities were observed for a significant number of compounds of this invention. The X substitutions were aromatic groups and also those in which the X aromatic group was additionally substituted with heterocyclic rings. The more active compounds had MICs against MDR-TB that were either less than one microgram/mL or significantly less than one microgram/mL.

We claim:

1. A compound according to Formula I, including tautomers, geometric isomers and pharmaceutically acceptable salts thereof Formula I

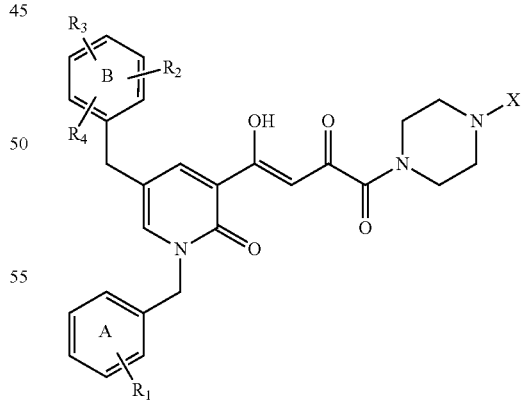

wherein R$_1$, R$_2$, R$_3$ and R$_4$ are each independently H or F; and

X is a phenyl group which is optionally substituted with dimethylamine or a nitrogen containing heterocyclic group selected from the group consisting of pyrrolyl, imidazolyl, pyrazolyl and triazolyl, or X is a biphenyl, naphthyl, anthracenyl or phenanthryl group.

2. A compound according to claim 1 wherein
$R_1$=H, $R_2$=H, $R_3$=H, $R_4$=H;
$R_1$=H, $R_2$=o-F, $R_3$=o-F, $R_4$=p-F;
$R_1$=o-F, $R_2$=o-F, $R_3$=o-F, $R_4$=m-F;
$R_1$=o-F, $R_2$=o-F, $R_3$=o-F, $R_4$=p-F
$R_1$=o-F, $R_2$=o-F, $R_3$=m-F, $R_4$=m-F;
$R_1$=o-F, $R_2$=o-F, $R_3$=m-F, $R_4$=p-F
$R_1$=o-F, $R_2$=m-F, $R_3$=m-F, $R_4$=p-F;
$R_1$=H, $R_2$=m-F, $R_3$=m-F, $R_4$=p-F;
$R_1$=m-F, $R_2$=o-F, $R_3$=o-F, $R_4$=m-F;
$R_1$=m-F, $R_2$=o-F, $R_3$=o-F, $R_4$=p-F;
$R_1$=m-F, $R_2$=o-F, $R_3$=m-F, $R_4$=m-F;
$R_1$=m-F, $R_2$=o-F, $R_3$=m-F, $R_4$=p-F;
$R_1$=m-F, $R_2$=o-F, $R_3$=m-F, $R_4$=p-F
$R_1$=H, $R_2$=o-F, $R_3$=o-F, $R_4$=m-F;
$R_1$=p-F, $R_2$=o-F, $R_3$=o-F, $R_4$=m-F;
$R_1$=p-F, $R_2$=o-F, $R_3$=o-F, $R_4$=p-F;
$R_1$=p-F, $R_2$=o-F, $R_3$=m-F, $R_4$=m-F;
$R_1$=p-F, $R_2$=o-F, $R_3$=m-F, $R_4$=p-F;
$R_1$=p-F, $R_2$=m-F, $R_3$=m-F, $R_4$=p-F;
$R_1$=o-F, $R_2$=m-F, $R_3$=m-F, $R_4$=H;
$R_1$=o-F, $R_2$=p-F, $R_3$=H, $R_4$=H or
$R_1$=o-F, $R_2$=o-F, $R_3$=o-F, $R_4$=H.

3. A compound according to claim 1 wherein X is

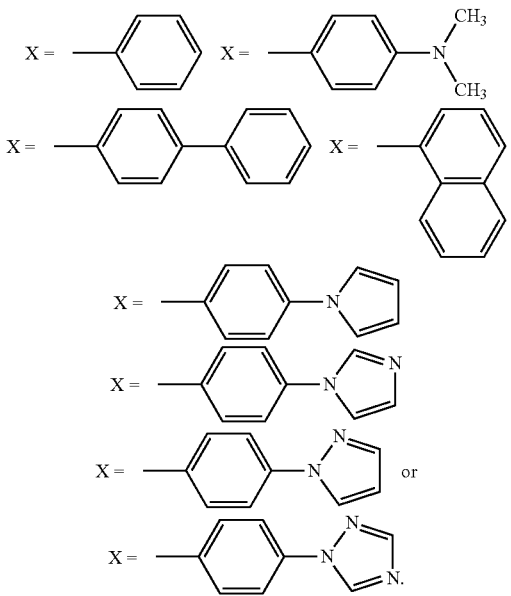

4. A compound according to claim 1 wherein X is a phenyl group or a naphthyl, anthracenyl or phenanthryl group.

5. The compound according to claim 1 wherein X is a phenyl group which is substituted with a dimethylamine or a nitrogen-containing heterocyclic group selected from the group consisting of pyrrolyl, imidazolyl, pyrazolyl and triazolyl and wherein said pyrrolyl group is a 1H-pyrrol-1-yl group, said imidazolyl group is a 1H-imidazol-1-yl group, said pyrazolyl group is a 1H-pyrazol-1-yl group and said triazolyl group is a 1H-1,2,4-triazolyl group.

6. The compound according to claim 5 wherein said nitrogen-containing heterocyclic group is selected from the group consisting of 1H-pyrrol-1-yl group, a 1H-imidazol-1-yl group and a 1H-pyrazol-1-yl group.

7. The compound according to claim 5 wherein said nitrogen-containing group is a 1H-1,2,4-triazolyl group.

8. The compound according to claim 1 which is:
4-(1,5-dibenzyl-2-oxo-1,2-dihydropyridin-3-yl)-4-hydroxy-1-(4-phenylpiperazin-1-yl)but-3-ene-1,2-dione;
1-(4-([1,1'-biphenyl]-4-yl)piperazin-1-yl)-4-(1,5-dibenzyl-2-oxo-1,2-dihydropyridin-3-yl)-4-hydroxybut-3-ene-1,2-dione;
4-(1,5-dibenzyl-2-oxo-1,2-dihydropyridin-3-yl)-4-hydroxy-1-(4-(naphthalen-1-yl)piperazin-1-yl)but-3-ene-1,2-dione;
4-(1,5-dibenzyl-2-oxo-1,2-dihydropyridin-3-yl)-1-(4-(4-(dimethylamino)phenyl)piperazin-1-yl)-4-hydroxybut-3-ene-1,2-dione;
1-(4-(4-(1H-pyrrol-1-yl)phenyl)piperazin-1-yl)-4-(1,5-dibenzyl-2-oxo-1,2-dihydropyridin-3-yl)-4-hydroxybut-3-ene-1,2-dione;
1-(4-(4-(1H-imidazol-1-yl)phenyl)piperazin-1-yl)-4-(1,5-dibenzyl-2-oxo-1,2-dihydropyridin-3-yl)-4-hydroxybut-3-ene-1,2-dione;
1-(4-(4-(1H-pyrazol-1-yl)phenyl)piperazin-1-yl)-4-(1,5-dibenzyl-2-oxo-1,2-dihydropyridin-3-yl)-4-hydroxybut-3-ene-1,2-dione;
1-(4-(4-(1H-1,2,4-triazol-1-yl)phenyl)piperazin-1-yl)-4-(1,5-dibenzyl-2-oxo-1,2-dihydropyridin-3-yl)-4-hydroxybut-3-ene-1,2-dione;
4-(1-(2-fluorobenzyl)-5-(4-fluorobenzyl)-2-oxo-1,2-dihydropyridin-3-yl)-4-hydroxy-1-(4-phenylpiperazin-1-yl)but-3-ene-1,2-dione;
1-(4-([1,1'-biphenyl]-4-yl)piperazin-1-yl)-4-(1-(2-fluorobenzyl)-5-(4-fluorobenzyl)-2-oxo-1,2-dihydropyridin-3-yl)-4-hydroxybut-3-ene-1,2-dione;
4-(1-(2-fluorobenzyl)-5-(4-fluorobenzyl)-2-oxo-1,2-dihydropyridin-3-yl)-4-hydroxy-1-(4-(naphthalen-1-yl)piperazin-1-yl)but-3-ene-1,2-dione;
1-(4-(4-(dimethylamino)phenyl)piperazin-1-yl)-4-(1-(2-fluorobenzyl)-5-(4-fluorobenzyl)-2-oxo-1,2-dihydropyridin-3-yl)-4-hydroxybut-3-ene-1,2-dione;
1-(4-(4-(1H-pyrrol-1-yl)phenyl)piperazin-1-yl)-4-(1-(2-fluorobenzyl)-5-(4-fluorobenzyl)-2-oxo-1,2-dihydropyridin-3-yl)-4-hydroxybut-3-ene-1,2-dione;
1-(4-(4-(1H-imidazol-1-yl)phenyl)piperazin-1-yl)-4-(1-(2-fluorobenzyl)-5-(4-fluorobenzyl)-2-oxo-1,2-dihydropyridin-3-yl)-4-hydroxybut-3-ene-1,2-dione;
1-(4-(4-(1H-pyrazol-1-yl)phenyl)piperazin-1-yl)-4-(1-(2-fluorobenzyl)-5-(4-fluorobenzyl)-2-oxo-1,2-dihydropyridin-3-yl)-4-hydroxybut-3-ene-1,2-dione;
1-(4-(4-(1H-1,2,4-triazol-1-yl)phenyl)piperazin-1-yl)-4-(1-(2-fluorobenzyl)-5-(4-fluorobenzyl)-2-oxo-1,2-dihydropyridin-3-yl)-4-hydroxybut-3-ene-1,2-dione;
4-(5-(2,6-difluorobenzyl)-1-(2-fluorobenzyl)-2-oxo-1,2-dihydropyridin-3-yl)-4-hydroxy-1-(4-(naphthalen-1-yl)piperazin-1-yl)but-3-ene-1,2-dione;
4-(5-(2,6-difluorobenzyl)-1-(2-fluorobenzyl)-2-oxo-1,2-dihydropyridin-3-yl)-4-hydroxy-1-(4-phenylpiperazin-1-yl)but-3-ene-1,2-dione;
1-(4-([1,1'-biphenyl]-4-yl)piperazin-1-yl)-4-(5-(2,6-difluorobenzyl)-1-(2-fluorobenzyl)-2-oxo-1,2-dihydropyridin-3-yl)-4-hydroxybut-3-ene-1,2-dione;
4-(5-(2,6-difluorobenzyl)-1-(2-fluorobenzyl)-2-oxo-1,2-dihydropyridin-3-yl)-1-(4-(4-(dimethylamino)phenyl)piperazin-1-yl)-4-hydroxybut-3-ene-1,2-dione;
1-(4-(4-(1H-pyrrol-1-yl)phenyl)piperazin-1-yl)-4-(5-(2,6-difluorobenzyl)-1-(2-fluorobenzyl)-2-oxo-1,2-dihydropyridin-3-yl)-4-hydroxybut-3-ene-1,2-dione;
1-(4-(4-(1H-imidazol-1-yl)phenyl)piperazin-1-yl)-4-(5-(2,6-difluorobenzyl)-1-(2-fluorobenzyl)-2-oxo-1,2-dihydropyridin-3-yl)-4-hydroxybut-3-ene-1,2-dione;

1-(4-(4-(1H-pyrazol-1-yl)phenyl)piperazin-1-yl)-4-(5-(2,6-difluorobenzyl)-1-(2-fluorobenzyl)-2-oxo-1,2-dihydropyridin-3-yl)-4-hydroxybut-3-ene-1,2-dione;

1-(4-(4-(1H-1,2,4-triazol-1-yl)phenyl)piperazin-1-yl)-4-(5-(2,6-difluorobenzyl)-1-(2-fluorobenzyl)-2-oxo-1,2-dihydropyridin-3-yl)-4-hydroxybut-3-ene-1,2-dione;

4-(5-(3,5-difluorobenzyl)-1-(2-fluorobenzyl)-2-oxo-1,2-dihydropyridin-3-yl)-4-hydroxy-1-(4-phenylpiperazin-1-yl)but-3-ene-1,2-dione;

1-(4-([1,1'-biphenyl]-4-yl)piperazin-1-yl)-4-(5-(3,5-difluorobenzyl)-1-(2-fluorobenzyl)-2-oxo-1,2-dihydropyridin-3-yl)-4-hydroxybut-3-ene-1,2-dione;

4-(5-(3,5-difluorobenzyl)-1-(2-fluorobenzyl)-2-oxo-1,2-dihydropyridin-3-yl)-4-hydroxy-1-(4-(naphthalen-1-yl)piperazin-1-yl)but-3-ene-1,2-dione;

1-(4-(5-(3,5-difluorobenzyl)-1-(2-fluorobenzyl)-2-oxo-1,2-dihydropyridin-3-yl)-1-(4-(4-(dimethylamino)phenyl)piperazin-1-yl)-4-hydroxybut-3-ene-1,2-dione;

1-(4-(4-(1H-pyrrol-1-yl)phenyl)piperazin-1-yl)-4-(5-(3,5-difluorobenzyl)-1-(2-fluorobenzyl)-2-oxo-1,2-dihydropyridin-3-yl)-4-hydroxybut-3-ene-1,2-dione;

1-(4-(4-(1H-imidazol-1-yl)phenyl)piperazin-1-yl)-4-(5-(3,5-difluorobenzyl)-1-(2-fluorobenzyl)-2-oxo-1,2-dihydropyridin-3-yl)-4-hydroxybut-3-ene-1,2-dione;

1-(4-(4-(1H-pyrazol-1-yl)phenyl)piperazin-1-yl)-4-(5-(3,5-difluorobenzyl)-1-(2-fluorobenzyl)-2-oxo-1,2-dihydropyridin-3-yl)-4-hydroxybut-3-ene-1,2-dione;

1-(4-(4-(1H-1,2,4-triazol-1-yl)phenyl)piperazin-1-yl)-4-(5-(3,5-difluorobenzyl)-1-(2-fluorobenzyl)-2-oxo-1,2-dihydropyridin-3-yl)-4-hydroxybut-3-ene-1,2-dione;

4-(1-benzyl-2-oxo-5-(2,4,6-trifluorobenzyl)-1,2-dihydropyridin-3-yl)-4-hydroxy-1-(4-phenylpiperazin-1-yl)but-3-ene-1,2-dione;

1-(4-([1,1'-biphenyl]-4-yl)piperazin-1-yl)-4-(1-benzyl-2-oxo-5-(2,4,6-trifluorobenzyl)-1,2-dihydropyridin-3-yl)-4-hydroxybut-3-ene-1,2-dione;

4-(1-benzyl-2-oxo-5-(2,4,6-trifluorobenzyl)-1,2-dihydropyridin-3-yl)-4-hydroxy-1-(4-(naphthalen-1-yl)piperazin-1-yl)but-3-ene-1,2-dione;

4-(1-benzyl-2-oxo-5-(2,4,6-trifluorobenzyl)-1,2-dihydropyridin-3-yl)-1-(4-(4-(dimethylamino)phenyl)piperazin-1-yl)-4-hydroxybut-3-ene-1,2-dione;

1-(4-(4-(1H-pyrrol-1-yl)phenyl)piperazin-1-yl)-4-(1-benzyl-2-oxo-5-(2,4,6-trifluorobenzyl)-1,2-dihydropyridin-3-yl)-4-hydroxybut-3-ene-1,2-dione;

1-(4-(4-(1H-imidazol-1-yl)phenyl)piperazin-1-yl)-4-(1-benzyl-2-oxo-5-(2,4,6-trifluorobenzyl)-1,2-dihydropyridin-3-yl)-4-hydroxybut-3-ene-1,2-dione;

1-(4-(4-(1H-pyrazol-1-yl)phenyl)piperazin-1-yl)-4-(1-benzyl-2-oxo-5-(2,4,6-trifluorobenzyl)-1,2-dihydropyridin-3-yl)-4-hydroxybut-3-ene-1,2-dione;

1-(4-(4-(1H-1,2,4-triazol-1-yl)phenyl)piperazin-1-yl)-4-(1-benzyl-2-oxo-5-(2,4,6-trifluorobenzyl)-1,2-dihydropyridin-3-yl)-4-hydroxybut-3-ene-1,2-dione;

4-(1-(2-fluorobenzyl)-2-oxo-5-(2,4,6-trifluorobenzyl)-1,2-dihydropyridin-3-yl)-4-hydroxy-1-(4-phenylpiperazin-1-yl)but-3-ene-1,2-dione;

1-(4-([1,1'-biphenyl]-4-yl)piperazin-1-yl)-4-(1-(2-fluorobenzyl)-2-oxo-5-(2,4,6-trifluorobenzyl)-1,2-dihydropyridin-3-yl)-4-hydroxybut-3-ene-1,2-dione;

4-(1-(2-fluorobenzyl)-2-oxo-5-(2,4,6-trifluorobenzyl)-1,2-dihydropyridin-3-yl)-4-hydroxy-1-(4-(naphthalen-1-yl)piperazin-1-yl)but-3-ene-1,2-dione;

1-(4-(4-(dimethylamino)phenyl)piperazin-1-yl)-4-(1-(2-fluorobenzyl)-2-oxo-5-(2,4,6-trifluorobenzyl)-1,2-dihydropyridin-3-yl)-4-hydroxybut-3-ene-1,2-dione;

1-(4-(4-(1H-pyrrol-1-yl)phenyl)piperazin-1-yl)-4-(1-(2-fluorobenzyl)-2-oxo-5-(2,4,6-trifluorobenzyl)-1,2-dihydropyridin-3-yl)-4-hydroxybut-3-ene-1,2-dione;

1-(4-(4-(1H-imidazol-1-yl)phenyl)piperazin-1-yl)-4-(1-(2-fluorobenzyl)-2-oxo-5-(2,4,6-trifluorobenzyl)-1,2-dihydropyridin-3-yl)-4-hydroxybut-3-ene-1,2-dione;

1-(4-(4-(1H-pyrazol-1-yl)phenyl)piperazin-1-yl)-4-(1-(2-fluorobenzyl)-2-oxo-5-(2,4,6-trifluorobenzyl)-1,2-dihydropyridin-3-yl)-4-hydroxybut-3-ene-1,2-dione;

1-(4-(4-(1H-1,2,4-triazol-1-yl)phenyl)piperazin-1-yl)-4-(1-(2-fluorobenzyl)-2-oxo-5-(2,4,6-trifluorobenzyl)-1,2-dihydropyridin-3-yl)-4-hydroxybut-3-ene-1,2-dione;

4-(1-(4-fluorobenzyl)-2-oxo-5-(2,4,6-trifluorobenzyl)-1,2-dihydropyridin-3-yl)-4-hydroxy-1-(4-phenylpiperazin-1-yl)but-3-ene-1,2-dione;

1-(4-([1,1'-biphenyl]-4-yl)piperazin-1-yl)-4-(1-(4-fluorobenzyl)-2-oxo-5-(2,4,6-trifluorobenzyl)-1,2-dihydropyridin-3-yl)-4-hydroxybut-3-ene-1,2-dione;

4-(1-(4-fluorobenzyl)-2-oxo-5-(2,4,6-trifluorobenzyl)-1,2-dihydropyridin-3-yl)-4-hydroxy-1-(4-(naphthalen-1-yl)piperazin-1-yl)but-3-ene-1,2-dione;

1-(4-(4-(dimethylamino)phenyl)piperazin-1-yl)-4-(1-(4-fluorobenzyl)-2-oxo-5-(2,4,6-trifluorobenzyl)-1,2-dihydropyridin-3-yl)-4-hydroxybut-3-ene-1,2-dione;

1-(4-(4-(1H-pyrrol-1-yl)phenyl)piperazin-1-yl)-4-(1-(4-fluorobenzyl)-2-oxo-5-(2,4,6-trifluorobenzyl)-1,2-dihydropyridin-3-yl)-4-hydroxybut-3-ene-1,2-dione;

1-(4-(4-(1H-imidazol-1-yl)phenyl)piperazin-1-yl)-4-(1-(4-fluorobenzyl)-2-oxo-5-(2,4,6-trifluorobenzyl)-1,2-dihydropyridin-3-yl)-4-hydroxybut-3-ene-1,2-dione;

1-(4-(4-(1H-pyrazol-1-yl)phenyl)piperazin-1-yl)-4-(1-(4-fluorobenzyl)-2-oxo-5-(2,4,6-trifluorobenzyl)-1,2-dihydropyridin-3-yl)-4-hydroxybut-3-ene-1,2-dione; or 1-(4-(4-(1H-1,2,4-triazol-1-yl)phenyl)piperazin-1-yl)-4-(1-(4-fluorobenzyl)-2-oxo-5-(2,4,6-trifluorobenzyl)-1,2-dihydropyridin-3-yl)-4-hydroxybut-3-ene-1,2-dione.

9. The compound according to claim 1 which is:

4-(1-(2-fluorobenzyl)-2-oxo-5-(2,3,6-trifluorobenzyl)-1,2-dihydropyridin-3-yl)-4-hydroxy-1-(4-phenylpiperazin-1-yl)but-3-ene-1,2-dione;

1-(4-([1,1'-biphenyl]-4-yl)piperazin-1-yl)-4-(1-(2-fluorobenzyl)-2-oxo-5-(2,3,6-trifluorobenzyl)-1,2-dihydropyridin-3-yl)-4-hydroxybut-3-ene-1,2-dione;

4-(1-(2-fluorobenzyl)-2-oxo-5-(2,3,6-trifluorobenzyl)-1,2-dihydropyridin-3-yl)-4-hydroxy-1-(4-(naphthalen-1-yl)piperazin-1-yl)but-3-ene-1,2-dione;

1-(4-(4-(dimethylamino)phenyl)piperazin-1-yl)-4-(1-(2-fluorobenzyl)-2-oxo-5-(2,3,6-trifluorobenzyl)-1,2-dihydropyridin-3-yl)-4-hydroxybut-3-ene-1,2-dione;

1-(4-(4-(1H-pyrrol-1-yl)phenyl)piperazin-1-yl)-4-(1-(2-fluorobenzyl)-2-oxo-5-(2,3,6-trifluorobenzyl)-1,2-dihydropyridin-3-yl)-4-hydroxybut-3-ene-1,2-dione;

1-(4-(4-(1H-imidazol-1-yl)phenyl)piperazin-1-yl)-4-(1-(2-fluorobenzyl)-2-oxo-5-(2,3,6-trifluorobenzyl)-1,2-dihydropyridin-3-yl)-4-hydroxybut-3-ene-1,2-dione;

1-(4-(4-(1H-pyrazol-1-yl)phenyl)piperazin-1-yl)-4-(1-(2-fluorobenzyl)-2-oxo-5-(2,3,6-trifluorobenzyl)-1,2-dihydropyridin-3-yl)-4-hydroxybut-3-ene-1,2-dione;

1-(4-(4-(1H-1,2,4-triazol-1-yl)phenyl)piperazin-1-yl)-4-(1-(2-fluorobenzyl)-2-oxo-5-(2,3,6-trifluorobenzyl)-1,2-dihydropyridin-3-yl)-4-hydroxybut-3-ene-1,2-dione;

4-(1-(2-fluorobenzyl)-2-oxo-5-(2,3,5-trifluorobenzyl)-1,2-dihydropyridin-3-yl)-4-hydroxy-1-(4-phenylpiperazin-1-yl)but-3-ene-1,2-dione;

1-(4-([1,1'-biphenyl]-4-yl)piperazin-1-yl)-4-(1-(2-fluorobenzyl)-2-oxo-5-(2,3,5-trifluorobenzyl)-1,2-dihydropyridin-3-yl)-4-hydroxybut-3-ene-1,2-dione;

4-(1-(2-fluorobenzyl)-2-oxo-5-(2,3,5-trifluorobenzyl)-1,2-dihydropyridin-3-yl)-4-hydroxy-1-(4-(naphthalen-1-yl)piperazin-1-yl)but-3-ene-1,2-dione;
1-(4-(4-(dimethylamino)phenyl)piperazin-1-yl)-4-(1-(2-fluorobenzyl)-2-oxo-5-(2,3,5-trifluorobenzyl)-1,2-dihydropyridin-3-yl)-4-hydroxybut-3-ene-1,2-dione;
1-(4-(4-(1H-pyrrol-1-yl)phenyl)piperazin-1-yl)-4-(1-(2-fluorobenzyl)-2-oxo-5-(2,3,5-trifluorobenzyl)-1,2-dihydropyridin-3-yl)-4-hydroxybut-3-ene-1,2-dione;
1-(4-(4-(1H-imidazol-1-yl)phenyl)piperazin-1-yl)-4-(1-(2-fluorobenzyl)-2-oxo-5-(2,3,5-trifluorobenzyl)-1,2-dihydropyridin-3-yl)-4-hydroxybut-3-ene-1,2-dione;
1-(4-(4-(1H-pyrazol-1-yl)phenyl)piperazin-1-yl)-4-(1-(2-fluorobenzyl)-2-oxo-5-(2,3,5-trifluorobenzyl)-1,2-dihydropyridin-3-yl)-4-hydroxybut-3-ene-1,2-dione;
1-(4-(4-(1H-1,2,4-triazol-1-yl)phenyl)piperazin-1-yl)-4-(1-(2-fluorobenzyl)-2-oxo-5-(2,3,5-trifluorobenzyl)-1,2-dihydropyridin-3-yl)-4-hydroxybut-3-ene-1,2-dione;
4-(1-(2-fluorobenzyl)-2-oxo-5-(2,3,4-trifluorobenzyl)-1,2-dihydropyridin-3-yl)-4-hydroxy-1-(4-phenylpiperazin-1-yl)but-3-ene-1,2-dione;
1-(4-([1,1'-biphenyl]-4-yl)piperazin-1-yl)-4-(1-(2-fluorobenzyl)-2-oxo-5-(2,3,4-trifluorobenzyl)-1,2-dihydropyridin-3-yl)-4-hydroxybut-3-ene-1,2-dione;
4-(1-(2-fluorobenzyl)-2-oxo-5-(2,3,4-trifluorobenzyl)-1,2-dihydropyridin-3-yl)-4-hydroxy-1-(4-(naphthalen-1-yl)piperazin-1-yl)but-3-ene-1,2-dione;
1-(4-(4-(dimethylamino)phenyl)piperazin-1-yl)-4-(1-(2-fluorobenzyl)-2-oxo-5-(2,3,4-trifluorobenzyl)-1,2-dihydropyridin-3-yl)-4-hydroxybut-3-ene-1,2-dione;
1-(4-(4-(1H-pyrrol-1-yl)phenyl)piperazin-1-yl)-4-(1-(2-fluorobenzyl)-2-oxo-5-(2,3,4-trifluorobenzyl)-1,2-dihydropyridin-3-yl)-4-hydroxybut-3-ene-1,2-dione;
1-(4-(4-(1H-imidazol-1-yl)phenyl)piperazin-1-yl)-4-(1-(2-fluorobenzyl)-2-oxo-5-(2,3,4-trifluorobenzyl)-1,2-dihydropyridin-3-yl)-4-hydroxybut-3-ene-1,2-dione;
1-(4-(4-(1H-pyrazol-1-yl)phenyl)piperazin-1-yl)-4-(1-(2-fluorobenzyl)-2-oxo-5-(2,3,4-trifluorobenzyl)-1,2-dihydropyridin-3-yl)-4-hydroxybut-3-ene-1,2-dione;
1-(4-(4-(1H-1,2,4-triazol-1-yl)phenyl)piperazin-1-yl)-4-(1-(2-fluorobenzyl)-2-oxo-5-(2,3,4-trifluorobenzyl)-1,2-dihydropyridin-3-yl)-4-hydroxybut-3-ene-1,2-dione;
4-(1-(2-fluorobenzyl)-2-oxo-5-(3,4,5-trifluorobenzyl)-1,2-dihydropyridin-3-yl)-4-hydroxy-1-(4-phenylpiperazin-1-yl)but-3-ene-1,2-dione; or
1-(4-([1,1'-biphenyl]-4-yl)piperazin-1-yl)-4-(1-(2-fluorobenzyl)-2-oxo-5-(3,4,5-trifluorobenzyl)-1,2-dihydropyridin-3-yl)-4-hydroxybut-3-ene-1,2-dione.

10. The compound according to claim 1 which is:
4-(1-(2-fluorobenzyl)-2-oxo-5-(3,4,5-trifluorobenzyl)-1,2-dihydropyridin-3-yl)-4-hydroxy-1-(4-(naphthalen-1-yl)piperazin-1-yl)but-3-ene-1,2-dione;
1-(4-(4-(dimethylamino)phenyl)piperazin-1-yl)-4-(1-(2-fluorobenzyl)-2-oxo-5-(3,4,5-trifluorobenzyl)-1,2-dihydropyridin-3-yl)-4-hydroxybut-3-ene-1,2-dione;
1-(4-(4-(1H-pyrrol-1-yl)phenyl)piperazin-1-yl)-4-(1-(2-fluorobenzyl)-2-oxo-5-(3,4,5-trifluorobenzyl)-1,2-dihydropyridin-3-yl)-4-hydroxybut-3-ene-1,2-dione;
1-(4-(4-(1H-imidazol-1-yl)phenyl)piperazin-1-yl)-4-(1-(2-fluorobenzyl)-2-oxo-5-(3,4,5-trifluorobenzyl)-1,2-dihydropyridin-3-yl)-4-hydroxybut-3-ene-1,2-dione;
1-(4-(4-(1H-pyrazol-1-yl)phenyl)piperazin-1-yl)-4-(1-(2-fluorobenzyl)-2-oxo-5-(3,4,5-trifluorobenzyl)-1,2-dihydropyridin-3-yl)-4-hydroxybut-3-ene-1,2-dione;
1-(4-(4-(1H-1,2,4-triazol-1-yl)phenyl)piperazin-1-yl)-4-(1-(2-fluorobenzyl)-2-oxo-5-(3,4,5-trifluorobenzyl)-1,2-dihydropyridin-3-yl)-4-hydroxybut-3-ene-1,2-dione;
4-(1-benzyl-2-oxo-5-(3,4,5-trifluorobenzyl)-1,2-dihydropyridin-3-yl)-4-hydroxy-1-(4-phenylpiperazin-1-yl)but-3-ene-1,2-dione;
1-(4-([1,1'-biphenyl]-4-yl)piperazin-1-yl)-4-(1-benzyl-2-oxo-5-(3,4,5-trifluorobenzyl)-1,2-dihydropyridin-3-yl)-4-hydroxybut-3-ene-1,2-dione;
4-(1-benzyl-2-oxo-5-(3,4,5-trifluorobenzyl)-1,2-dihydropyridin-3-yl)-4-hydroxy-1-(4-(naphthalen-1-yl)piperazin-1-yl)but-3-ene-1,2-dione;
4-(1-benzyl-2-oxo-5-(3,4,5-trifluorobenzyl)-1,2-dihydropyridin-3-yl)-1-(4-(4-(dimethylamino)phenyl)piperazin-1-yl)-4-hydroxybut-3-ene-1,2-dione;
1-(4-(4-(1H-pyrrol-1-yl)phenyl)piperazin-1-yl)-4-(1-benzyl-2-oxo-5-(3,4,5-trifluorobenzyl)-1,2-dihydropyridin-3-yl)-4-hydroxybut-3-ene-1,2-dione;
1-(4-(4-(1H-imidazol-1-yl)phenyl)piperazin-1-yl)-4-(1-benzyl-2-oxo-5-(3,4,5-trifluorobenzyl)-1,2-dihydropyridin-3-yl)-4-hydroxybut-3-ene-1,2-dione;
1-(4-(4-(1H-pyrazol-1-yl)phenyl)piperazin-1-yl)-4-(1-benzyl-2-oxo-5-(3,4,5-trifluorobenzyl)-1,2-dihydropyridin-3-yl)-4-hydroxybut-3-ene-1,2-dione;
1-(4-(4-(1H-1,2,4-triazol-1-yl)phenyl)piperazin-1-yl)-4-(1-benzyl-2-oxo-5-(3,4,5-trifluorobenzyl)-1,2-dihydropyridin-3-yl)-4-hydroxybut-3-ene-1,2-dione;
4-(1-(3-fluorobenzyl)-2-oxo-5-(2,3,6-trifluorobenzyl)-1,2-dihydropyridin-3-yl)-4-hydroxy-1-(4-phenylpiperazin-1-yl)but-3-ene-1,2-dione;
1-(4-([1,1'-biphenyl]-4-yl)piperazin-1-yl)-4-(1-(3-fluorobenzyl)-2-oxo-5-(2,3,6-trifluorobenzyl)-1,2-dihydropyridin-3-yl)-4-hydroxybut-3-ene-1,2-dione;
4-(1-(3-fluorobenzyl)-2-oxo-5-(2,3,6-trifluorobenzyl)-1,2-dihydropyridin-3-yl)-4-hydroxy-1-(4-(naphthalene-1-yl)piperazin-1-yl)but-3-ene-1,2-dione;
1-(4-(4-(dimethylamino)phenyl)piperazin-1-yl)-4-(1-(3-fluorobenzyl)-2-oxo-5-(2,3,6-trifluorobenzyl)-1,2-dihydropyridin-3-yl)-4-hydroxybut-3-ene-1,2-dione, or
1-(4-(4-(1H-pyrrol-1-yl)phenyl)piperazin-1-yl)-4-(1-(3-fluorobenzyl)-2-oxo-5-(2,3,6-trifluorobenzyl)-1,2-dihydropyridin-3-yl)-4-hydroxybut-3-ene-1,2-dione.

11. The compound according to claim 1 which is:
1-(4-(4-(1H-imidazol-1-yl)phenyl)piperazin-1-yl)-4-(1-(3-fluorobenzyl)-2-oxo-5-(2,3,6-trifluorobenzyl)-1,2-dihydropyridin-3-yl)-4-hydroxybut-3-ene-1,2-dione;
1-(4-(4-(1H-pyrazol-1-yl)phenyl)piperazin-1-yl)-4-(1-(3-fluorobenzyl)-2-oxo-5-(2,3,6-trifluorobenzyl)-1,2-dihydropyridin-3-yl)-4-hydroxybut-3-ene-1,2-dione;
1-(4-(4-(1H-1,2,4-triazol-1-yl)phenyl)piperazin-1-yl)-4-(1-(3-fluorobenzyl)-2-oxo-5-(2,3,6-trifluorobenzyl)-1,2-dihydropyridin-3-yl)-4-hydroxybut-3-ene-1,2-dione;
4-(1-(3-fluorobenzyl)-2-oxo-5-(2,4,6-trifluorobenzyl)-1,2-dihydropyridin-3-yl)-4-hydroxy-1-(4-phenylpiperazin-1-yl)but-3-ene-1,2-dione;
1-(4-([1,1'-biphenyl]-4-yl)piperazin-1-yl)-4-(1-(3-fluorobenzyl)-2-oxo-5-(2,4,6-trifluorobenzyl)-1,2-dihydropyridin-3-yl)-4-hydroxybut-3-ene-1,2-dione;
4-(1-(3-fluorobenzyl)-2-oxo-5-(2,4,6-trifluorobenzyl)-1,2-dihydropyridin-3-yl)-4-hydroxy-1-(4-(naphthalene-1-yl)piperazin-1-yl)but-3-ene-1,2-dione;
1-(4-(4-(dimethylamino)phenyl)piperazin-1-yl)-4-(1-(3-fluorobenzyl)-2-oxo-5-(2,4,6-trifluorobenzyl)-1,2-dihydropyridin-3-yl)-4-hydroxybut-3-ene-1,2-dione;
1-(4-(4-(1H-pyrrol-1-yl)phenyl)piperazin-1-yl)-4-(1-(3-fluorobenzyl)-2-oxo-5-(2,4,6-trifluorobenzyl)-1,2-dihydropyridin-3-yl)-4-hydroxybut-3-ene-1,2-dione;
1-(4-(4-(1H-imidazol-1-yl)phenyl)piperazin-1-yl)-4-(1-(3-fluorobenzyl)-2-oxo-5-(2,4,6-trifluorobenzyl)-1,2-dihydropyridin-3-yl)-4-hydroxybut-3-ene-1,2-dione;

1-(4-(4-(1H-pyrazol-1-yl)phenyl)piperazin-1-yl)-4-(1-(3-fluorobenzyl)-2-oxo-5-(2,4,6-trifluorobenzyl)-1,2-dihydropyridin-3-yl)-4-hydroxybut-3-ene-1,2-dione;
1-(4-(4-(1H-1,2,4-triazol-1-yl)phenyl)piperazin-1-yl)-4-(1-(3-fluorobenzyl)-2-oxo-5-(2,4,6-trifluorobenzyl)-1,2-dihydropyridin-3-yl)-4-hydroxybut-3-ene-1,2-dione;
4-(1-(3-fluorobenzyl)-2-oxo-5-(2,3,5-trifluorobenzyl)-1,2-dihydropyridin-3-yl)-4-hydroxy-1-(4-phenylpiperazin-1-yl)but-3-ene-1,2-dione;
1-(4-([1,1'-biphenyl]-4-yl)piperazin-1-yl)-4-(1-(3-fluorobenzyl)-2-oxo-5-(2,3,5-trifluorobenzyl)-1,2-dihydropyridin-3-yl)-4-hydroxybut-3-ene-1,2-dione;
1-(4-(4-(dimethylamino)phenyl)piperazin-1-yl)-4-(1-(3-fluorobenzyl)-2-oxo-5-(2,3,5-trifluorobenzyl)-1,2-dihydropyridin-3-yl)-4-hydroxybut-3-ene-1,2-dione;
4-(1-(3-fluorobenzyl)-2-oxo-5-(2,3,5-trifluorobenzyl)-1,2-dihydropyridin-3-yl)-4-hydroxy-1-(4-(naphthalen-1-yl)piperazin-1-yl)but-3-ene-1,2-dione;
1-(4-(4-(1H-pyrrol-1-yl)phenyl)piperazin-1-yl)-4-(1-(3-fluorobenzyl)-2-oxo-5-(2,3,5-trifluorobenzyl)-1,2-dihydropyridin-3-yl)-4-hydroxybut-3-ene-1,2-dione;
1-(4-(4-(1H-imidazol-1-yl)phenyl)piperazin-1-yl)-4-(1-(3-fluorobenzyl)-2-oxo-5-(2,3,5-trifluorobenzyl)-1,2-dihydropyridin-3-yl)-4-hydroxybut-3-ene-1,2-dione;
1-(4-(4-(1H-pyrazol-1-yl)phenyl)piperazin-1-yl)-4-(1-(3-fluorobenzyl)-2-oxo-5-(2,3,5-trifluorobenzyl)-1,2-dihydropyridin-3-yl)-4-hydroxybut-3-ene-1,2-dione;
1-(4-(4-(1H-1,2,4-triazol-1-yl)phenyl)piperazin-1-yl)-4-(1-(3-fluorobenzyl)-2-oxo-5-(2,3,5-trifluorobenzyl)-1,2-dihydropyridin-3-yl)-4-hydroxybut-3-ene-1,2-dione;
4-(1-(3-fluorobenzyl)-2-oxo-5-(2,3,4-trifluorobenzyl)-1,2-dihydropyridin-3-yl)-4-hydroxy-1-(4-phenylpiperazin-1-yl)but-3-ene-1,2-dione;
1-(4-([1,1'-biphenyl]-4-yl)piperazin-1-yl)-4-(1-(3-fluorobenzyl)-2-oxo-5-(2,3,4-trifluorobenzyl)-1,2-dihydropyridin-3-yl)-4-hydroxybut-3-ene-1,2-dione;
4-(1-(3-fluorobenzyl)-2-oxo-5-(2,3,4-trifluorobenzyl)-1,2-dihydropyridin-3-yl)-4-hydroxy-1-(4-(naphthalen-1-yl)piperazin-1-yl)but-3-ene-1,2-dione;
1-(4-(4-(dimethylamino)phenyl)piperazin-1-yl)-4-(1-(3-fluorobenzyl)-2-oxo-5-(2,3,4-trifluorobenzyl)-1,2-dihydropyridin-3-yl)-4-hydroxybut-3-ene-1,2-dione;
1-(4-(4-(1H-pyrrol-1-yl)phenyl)piperazin-1-yl)-4-(1-(3-fluorobenzyl)-2-oxo-5-(2,3,4-trifluorobenzyl)-1,2-dihydropyridin-3-yl)-4-hydroxybut-3-ene-1,2-dione;
1-(4-(4-(1H-imidazol-1-yl)phenyl)piperazin-1-yl)-4-(1-(3-fluorobenzyl)-2-oxo-5-(2,3,4-trifluorobenzyl)-1,2-dihydropyridin-3-yl)-4-hydroxybut-3-ene-1,2-dione;
1-(4-(4-(1H-pyrazol-1-yl)phenyl)piperazin-1-yl)-4-(1-(3-fluorobenzyl)-2-oxo-5-(2,3,4-trifluorobenzyl)-1,2-dihydropyridin-3-yl)-4-hydroxybut-3-ene-1,2-dione; or
1-(4-(4-(1H-1,2,4-triazol-1-yl)phenyl)piperazin-1-yl)-4-(1-(3-fluorobenzyl)-2-oxo-5-(2,3,4-trifluorobenzyl)-1,2-dihydropyridin-3-yl)-4-hydroxybut-3-ene-1,2-dione.

12. A pharmaceutical composition for treating TB, MDR-TB or XDR-TB, comprising a therapeutic amount of a compound according to claim 1 in combination with a pharmaceutically acceptable carrier, additive or excipient.

13. The pharmaceutical composition of claim 12 wherein said composition treats said TB infection by inhibiting TB DNA-dependent RNA polymerase, both wild type and mutants, in the human host.

14. A pharmaceutical composition comprising a therapeutically effective amount of a compound according to claim 1, a pharmaceutically acceptable carrier, additive or excipient in combination with a therapeutically effective amount of at least one compound selected from the group consisting of: (i) another TB drug and/or a TB drug that is active against drug-resistant TB; (ii) a therapeutically effective amount of an agent for the treatment of AIDS; (iii) an anti-infective agent, (iv) an immunomodulator, (v) another bioactive agent selected from the group consisting of antibiotics, vaccines and an additional antiviral agent, and mixtures thereof.

15. The composition according to claim 12 in oral or parenteral dosage form.

16. The composition according to claim 12 formulated for administration as an inhalation spray or a rectal suppository.

17. A method of treating a TB infection in a patient, said method comprising administering to said patient an effective amount of a composition according to claim 12.

18. A method of treating a patient with TB comprising administering to said patient a therapeutically effective amount of a compound according to claim 1.

19. A method of inhibiting TB DNA-dependent RNA polymerase in a subject, said method comprising administering to said subject a therapeutically effective amount of a compound according to claim 1.

20. The method according to claim 17 wherein said subject is a human.

21. The method according to claim 17 wherein said TB infection is caused by TB which is drug-resistant.

22. The method according to claim 21 wherein said drug-resistant TB is extensively drug-resistant TB (XDR-TB).

23. The method according to claim 21 wherein said drug-resistant TB is extremely drug-resistant TB (XXDR-TB).

24. A pharmaceutical composition comprising an effective amount of a compound according to claim 1 in combination with an effective amount of at least one additional anti-TB agent and optionally at least one anti-HIV compound, in combination with a pharmaceutically acceptable carrier, additive or excipient.

25. The composition according to claim 24 wherein said anti-HIV compound is combined with an anti-infective agent.

26. The composition according to claim 24 wherein said anti-HIV compound treats said TB infection by inhibiting at least TB DNA-dependent RNA polymerase, both wild type and mutants, in the human host.

27. The composition according to claim 24 in oral or parenteral dosage form.

28. The composition according to claim 24 formulated for administration as an inhalation spray or a rectal suppository.

29. A method of treating a TB infection in a human host comprising administering to said host in combination, an effective amount of at least one compound according to claim 1 in combination with at least one anti-HIV agent and at least one other anti-TB compound in combination with a pharmaceutically acceptable carrier, additive or excipient.

30. A method of treating a TB infection in a patient, said method comprising administering to said patient an effective amount of a composition according to claim 24.

31. A method of inhibiting TB DNA-dependent RNA polymerase in a subject, said method comprising administering to said subject a therapeutically effective amount of a composition according to claim 24.

32. The method according to claim 30 wherein said patient is a human.

33. A kit comprising a pharmaceutical composition according to claim 12 and instructions for a medical professional and/or a patient on how to administer said composition.

* * * * *